United States Patent
Wang et al.

(10) Patent No.: US 10,533,037 B2
(45) Date of Patent: Jan. 14, 2020

(54) FREEZE-DRIED POWDER OF HIGH MOLECULAR WEIGHT SILK FIBROIN, PREPARATION METHOD THEREFOR AND USE THEREOF

(71) Applicant: SIMATECH INCORPORATION, Suzhou, Jiangsu (CN)

(72) Inventors: Xiaoqin Wang, Jiangsu (CN); Jian Liu, Jiangsu (CN); Jianbing Wu, Jiangsu (CN); Cheng Qian, Jiangsu (CN); Zhaozhu Zheng, Jiangsu (CN); Shaozhe Guo, Jiangsu (CN); Fuxin Shi, Jiangsu (CN); David Kaplan, Medford, MA (US)

(73) Assignees: SIMATECH INCORPORATION, Suzhou (CN); TRUSTEES OF TUFTS COLLEGE, Medford, MA (US)

( * ) Notice: Subject to any disclaimer, the term of this patent is extended or adjusted under 35 U.S.C. 154(b) by 0 days.

(21) Appl. No.: 15/129,246

(22) PCT Filed: Mar. 25, 2015

(86) PCT No.: PCT/CN2015/075019
§ 371 (c)(1),
(2) Date: Sep. 26, 2016

(87) PCT Pub. No.: WO2015/144056
PCT Pub. Date: Oct. 1, 2015

(65) Prior Publication Data
US 2017/0107264 A1  Apr. 20, 2017

(30) Foreign Application Priority Data

Mar. 27, 2014 (CN) .......................... 2014 1 0118409
Mar. 27, 2014 (CN) .......................... 2014 1 0118465
Dec. 16, 2014 (CN) .......................... 2014 1 0777934
Feb. 11, 2015 (CN) .......................... 2015 1 0071886
Feb. 27, 2015 (CN) .......................... 2015 1 0089733

(51) Int. Cl.
| | | |
|---|---|---|
| C07K 14/435 | (2006.01) |
| A61K 9/06 | (2006.01) |
| A61K 9/00 | (2006.01) |
| A61K 9/14 | (2006.01) |
| A61K 9/16 | (2006.01) |
| A61K 38/01 | (2006.01) |
| A61K 35/62 | (2006.01) |
| A61K 9/19 | (2006.01) |
| A61K 47/42 | (2017.01) |
| B01D 21/26 | (2006.01) |
| B01D 61/14 | (2006.01) |
| B01D 61/24 | (2006.01) |
| F26B 5/06 | (2006.01) |
| A61J 3/02 | (2006.01) |

(52) U.S. Cl.
CPC ...... *C07K 14/43586* (2013.01); *A61K 9/0046* (2013.01); *A61K 9/06* (2013.01); *A61K 9/143* (2013.01); *A61K 9/146* (2013.01); *A61K 9/1641* (2013.01); *A61K 9/19* (2013.01); *A61K 35/62* (2013.01); *A61K 38/012* (2013.01); *A61K 47/42* (2013.01); *B01D 21/262* (2013.01); *B01D 61/145* (2013.01); *B01D 61/243* (2013.01); *C07K 14/43504* (2013.01); *F26B 5/06* (2013.01); *A61J 3/02* (2013.01)

(58) Field of Classification Search
CPC .......................... C07K 14/43586; A61K 9/06
See application file for complete search history.

(56) References Cited

U.S. PATENT DOCUMENTS 5,252,285 A * 10/1993 Lock ........................ D01F 4/02
                                                      264/202

FOREIGN PATENT DOCUMENTS

| CN | 102430155 A | 5/2012 |
| CN | 103289107 A | 9/2013 |
| CN | 103910789 A | 7/2014 |

OTHER PUBLICATIONS

Wang, Sonication-induced gelation of silk fibroin for cell encapsulation, Biomaterials 29 (2008) 1054-1064.*
Rockwood, Materials fabrication from Bombyx mori silk fibroin, Nature Protocols, 2011 vol. 6 No. 10.*
Tsumoto, Practical considerations in refolding proteins from inclusion bodies, Protein Expression and Purification 28 (2003) 1-8.*
Wang, Sonication-induced gelation of silk fibroin for cell encapsulation, Biomaterials 29 (2008) 1054-1064, of record (Year: 2008).*
Rockwood, Materials fabrication from Bombyx mori silk fibroin, Nature Protocols, 2011 vol. 6 No. 10, of record (Year: 2011).*
Tsumoto, Practical considerations in refolding proteins from inclusion bodies, Protein Expression and Purification 28 (2003) 1-8, of record (Year: 2003).*

(Continued)

*Primary Examiner* — Karlheinz R. Skowronek
*Assistant Examiner* — Khalid Kader
(74) *Attorney, Agent, or Firm* — SZDC LAW P.C.

(57) ABSTRACT

The invention discloses a freeze-dried powder of high molecular weight silk fibroin, preparation process and use thereof. The freeze-dried powder is obtained from silk by degumming, dissolution, dialysis, centrifugation, high temperature and high pressure treatment and freeze-drying. A method of preparing silk fibroin microspheres with polyethylene glycol comprises mixing a silk fibroin solution of 1-30 wt % with a PEG solution of 10-60 w % and incubating the resulting solution. A controlled-release or sustained-release silk fibroin gel formulation includes a gel-state carrier and a drug dispersed/adsorbed therein, the carrier is a silk fibroin gel formed by blending with LMW-PEG. The freeze-dried powder will not change the native molecular weight and random coil structure of silk fibroin, and can be rapidly dissolved into a solution, and can be stored and transported for a long time, and this reduces waste of silk fibroin materials and promotes R & D and biomedical applications of silk fibroin biomaterials.

3 Claims, 20 Drawing Sheets

(56) References Cited

OTHER PUBLICATIONS

Tsumoto (Practical considerations in refolding proteins from inclusion bodies, Protein Expression and Purification 28 (2003) 1-8) (Year: 2003).*
Lu (Water-Insoluble Silk Films with Silk I Structure, Acta Biomater. Apr. 2010 ; 6(4): 1380-1387) (Year: 2010).*
Wang (Sonication-Induced Gelation of Silk Fibroin for Cell Encapsulation, Biomaterials 2008, 29: 1054-1064) (Year: 2008).*
Rockwood (Materials fabrication from Bombyx mori silk fibroin, Nature Protocols, 2011 vol. 6 No. 10) (Year: 2011).*
Pikal-Cleland (Effect of Glycine on pH Changes and Protein Stability during Freeze—Thawing in Phosphate Buffer Systems, Journal of Pharmaceutical Sciences 2002, vol. 91, No. 9) (Year: 2002).*
Wang, Lu et al., "Progress of Silk Fibroin Microspheres", Modern Silk Science and Technology, No. 6, Jun. 30, 2010 (Jun. 30, 2010), section 3.

* cited by examiner

FREEZE-DRIED POWDER OF HIGH MOLECULAR WEIGHT SILK FIBROIN, PREPARATION METHOD THEREFOR AND USE THEREOF

The present application is national phase application of PCT/CN2015/075019, filed on Mar. 25, 2015, which claims priority to Chinese Patent Application Nos. CN 2014-10118465.7, filed on Mar. 27, 2014, CN 201410118409.3, filed on Mar. 27, 2014, CN 201410777934.6, filed on Dec. 16, 2014, CN 201510071886.3, filed on Feb. 11, 2015, and CN 201510089733.1, filed on Feb. 27, 2015, all of which are incorporated by reference for all purposes as if fully set forth herein.

FIELD OF THE INVENTION

The present invention relates to the field of biological materials, and more particularly to a freeze-dried powder of high molecular weight silk fibroin, preparation process therefor and use thereof.

DESCRIPTION OF THE RELATED ART

In recent years, many biodegradable biological materials such as films, particles, porous scaffolds and hydrogels, made of a regenerated silk fibroin solution, have been shown to have excellent biocompatibility, non-immunogenicity and slow degradation. They are becoming a new medical biological material, and can be used as a product directly for clinical tissue repair or can be used as a carrier support of drugs and cells for sustained release of drugs and tissue engineering of artificial organs. Therefore, a silk fibroin solution is a basis for preparing all silk fibroin-based biological materials, and how to obtain a silk fibroin solution with high quality, high molecular weight, and high stability by purification is critical for further development of silk fibroin-based medical biological materials.

There are many conditions being used for preparing a high molecular weight regenerated silk fibroin, and two essential steps are dissolution of degummed silk and dialysis for removal of denaturants. The concentration of the aqueous silk fibroin solution obtained after dialysis is generally 4-10% (w/v). Because a change in a molecular structure of silk fibroin easily occurs at a high temperature, resulting in aggregation and thus gel formation or precipitation, the purified silk fibroin solution is usually stored in a refrigerator at 4° C. for no more than two months. The storage life at room temperature is no more than two weeks. This causes much inconvenience for downstream material preparation and application, mainly in that: (1) time and materials are wasted: re-purification of the silk fibroin solution is needed for each material preparation; (2) the product quality is difficult to control and the reproducibility is poor: for a high molecular weight silk fibroin solution, the structure of silk fibroin slowly changes even in a refrigerator at 4° C., and the molecules continuously aggregate, which may directly affect the performance of subsequent material preparation; and (3) storage and transportation are difficult: when a silk fibroin solution is marketed as a commodity directly or as a main component of, for example, an injectable gel, storage temperature and conditions need to be considered, which is a primary problem restricting its large scale application and development. In addition, a silk fibroin solution having a higher concentration is required for preparation and application of certain materials, and a desired high-concentration silk fibroin solution can only be obtained from the purified silk fibroin solution by further concentration processes such as polyethylene glycol dialysis and ultrafiltration, thereby resulting in additional costs and risk of contamination for material preparation.

SUMMARY OF THE INVENTION

In order to solve the above technical problems, an object of the present invention is to provide a preparation process of a freeze-dried powder of high molecular weight silk fibroin, and this process realizes rapid preparation, high controllability and reproducibility, as well as easy storage and transportation of freeze-dried powder.

1. In an aspect, the present invention provides a preparation process of a freeze-dried powder of high molecular weight silk fibroin, the process includes the following steps:

silk is boiled in an amount of a sodium carbonate solution for a period of time, and soaked and washed with clear water to give degummed silk, and after air drying, a suitable amount of the degummed silk is dissolved in a protein denaturant, such as a lithium bromide solution. After the degummed silk is completely dissolved, the resulting solution is dialyzed in a dialysis tube for two days, such that lithium bromide penetrates through the dialysis tube and silk fibroin is retained in the dialysis tube. Alternatively, lithium bromide is removed by ultrafiltration, the principle of which is similar to that of dialysis. Following dialysis or ultrafiltration, the silk fibroin solution is centrifuged, and the supernatant is taken as a silk fibroin solution. After the concentration of the solution is determined, it is mixed with a phosphate buffer solution to prepare a 3% w/v silk fibroin solution. By one step of high pressure and high temperature treatment, some silk fibroin molecules are induced to form stable nanoparticles while the molecular weight is not changed, and then a volume of the treated solution is transferred into a glass bottle and frozen overnight. After freeze-drying for a period of time, the freeze-dried powder of high molecular weight silk fibroin of the present invention is obtained.

Specific experimental steps include:

S1: silk degumming: 30 g silk is boiled in 25.44 g sodium carbonate/12 L deionized water for 0.5 h. Silk is continuously stirred during the boiling such that it is dispersed to prevent from being bonded together, and after the boiling, degummed silk is taken out, washed with deionized water three times to remove silk sericin, leaving silk fibroin, and the silk fibroin is dried on a laminar flow hood overnight;

S2: dissolution with lithium bromide: 10 g of the degummed silk is placed in 40 ml of a 9.3 M lithium bromide solution, and stirred with a glass rod such that the degummed silk is sufficiently impregnated, and then heated in an oven at 60° C. for 4 h;

S3: dialysis: dialysis is performed using a Pierce dialysis device having a molecular weight cut-off of 3500-10000 Daltons or a common dialysis tube for 36 h, and water is changed for 7 times at 3, 6, 12, 18, 24, 30, and 36 h of the dialysis, respectively, so that the lithium bromide salt is removed from the solution, leaving silk fibroin in the dialysis tube;

S4: centrifugation: the silk fibroin solution in the dialysis tube is transferred into a centrifuge container and centrifuged at 9000 rmp for 20 min at 4° C., the precipitate is discarded, and the supernatant solution is taken as the desired silk fibroin solution;

S5: concentration determination: an amount of the silk fibroin solution is dried over 3 h at 60° C., and the resulting silk fibroin membrane is weighed to obtain the concentration of the silk fibroin solution (w/v);

S6: high temperature and high pressure treatment: the silk fibroin solution is diluted with ultrapure water to a concentration of 6%, and the silk fibroin solution at a concentration of 6% is uniformly mixed with a 10 mM PB buffer having a pH=7.4 in a volume ratio of 1:1, so that the final concentration of the silk fibroin solution is 3% (w/v) and the final concentration of the PB buffer is 5 mM after mixing, and then the solution is transferred to a glass container and is subjected to high temperature and high pressure treatment at 121° C. and 0.1 Mpa for 20 min; and S7: freeze-drying: 10 ml of the sterilized solution is thoroughly frozen at a temperature of below −20° C. in a sterile, 15 ml glass bottle, and then evacuated in a lyophilizer over 48 h to induce ice sublimation, thereby getting the freeze-dried powder of high molecular weight silk fibroin.

Specifically, lithium bromide in S2 can be replaced with another compound, such as a calcium chloride/ethanol/water ternary mixture at a molar ratio of 1:2:8, lithium thiocyanate, and calcium chloride.

Specifically, the dialysis in S3 can be replaced with desalting column chromatography or ultrafiltration to remove lithium bromide or other salt ions. If desalting column chromatography is used in S3, then S4 can be omitted.

Specifically, the PB buffer in S6 can be replaced with another buffer capable of maintaining the stable pH, such as tris buffer, sodium acetate buffer, ammonium chloride buffer.

Specifically, the concentration and the volume ratio of the silk fibroin solution and the PB buffer in S6 can be varied, but in the mixture, the final concentration of the silk fibroin solution is not greater than 3% (w/v) and the final concentration of the PB buffer is not less than 5 mM.

Specifically, the temperature and the pressure and the time used to treat the silk fibroin solution in S6 can be varied, but the solution needs to be completely sterilized and the silk fibroin molecular weight and aggregation state (particle size) are not significantly affected by the treatment.

2. In another aspect, the present invention also provides a freeze-dried powder of high molecular weight silk fibroin obtained by the above preparation process, the freeze-dried powder can maintain the random coil molecular structure of silk fibroin during freezing and drying, such that it does not convert to the β-sheet structure or the degree of conversion is controlled, and undesired intermolecular interaction, aggregation and crystallization of silk fibroin can be effectively prevented. The silk fibroin freeze-dried powder of the present invention can be rapidly and completely dissolved in water at high concentration (>30%), and applied in various biomedical and clinical fields.

The freeze-dried powder of high molecular weight silk fibroin of the present invention is obtained from silk by degumming, dissolution with protein denaturant, dialysis, centrifugation, high temperature and high pressure treatment, as well as freeze-drying.

Specifically, the secondary structure of silk fibroin of the freeze-dried powder is dominated by random coils and α-helices. The average molecular weight of silk fibroin of the freeze-dried powder is greater than 100000 Daltons, and after purification some silk fibroin molecules are present in the solution as aggregated particles of 50-300 nm and the size of the nanoparticles remains the same before and after treatment and after dissolution of the freeze-dried powder. The number of nanoparticles increases after high temperature and high pressure treatment though, therefore minimizing undesired intermolecular interaction, aggregation and crystallization of silk fibroin during freeze-drying and rehydration process.

3. In still other aspect, the present invention also provides an improved method of preparing a silk fibroin solution by avoiding the use of lithium bromide, including the following steps:

(1) degumming: silkworm silk is degummed to remove silk sericin in an outer layer to get degummed silk;

2) silk dissolution: the degummed silk is dissolved with a calcium chloride-containing ternary solution to get a silk fibroin solution;

3) renaturation: the silk fibroin solution is sequentially dialyzed against protein denaturant solutions in a gradient from high concentration to low concentration, or the silk fibroin solution is directly diluted with water or a protein denaturant and then dialyzed against water or ultrafiltrated for desalting to give a silk fibroin solution; and 4) storage: the silk fibroin solution is stored.

Specifically, the protein denaturant is a calcium chloride-containing ternary solution, urea, SDS, or guanidine hydrochloride.

Specifically, the protein denaturant is a calcium chloride-containing ternary solution, the protein denaturant solutions have a dilution factor of above 10 times relative to the original solution, and the silk fibroin solution after each dialysis or ultrafiltration has a conductivity of below 100 μs.

Specifically, the diluent is ultrapure water, the dilution factor is above 10 times relative to the original solution, and the silk fibroin solution after each dialysis or ultrafiltration has a conductivity of below 100 μs.

Specifically, the protein denaturant is urea, the protein denaturant solutions includes urea solutions of a molar concentration of 4 M, 2 M and 1 M, and the duration of each dialysis of the silk fibroin solution is 1 to 5 h.

Specifically, the protein denaturant is SDS, the protein denaturant solutions includes SDS solutions of 2% and 1% by weight, and the duration of each dialysis of the silk fibroin solution is 1 to 5 h.

Specifically, the protein denaturant is guanidine hydrochloride, the protein denaturant solutions includes guanidine hydrochloride solutions of a molar concentration of 2 M and 1 M, and the duration of each dialysis of the silk fibroin solution is 1 to 5 h.

Preferably, the calcium chloride-containing ternary solution contains calcium chloride, water and ethanol at a molar ratio of 1:8:2, and the degummed silk is subjected to silk dissolution in a bath ratio of 1:10 to 1:50 at a temperature of 60 to 85° C. for 0.5 to 24 h.

Specifically, the degummed silk is subjected to silk dissolution for 0.5 to 2 h.

Preferably, for the storage in the step (4), the silk fibroin solution is centrifuged to remove insoluble substances and then stored in a refrigerator at a constant temperature.

4. Correspondingly, in a still more other aspect, the present invention also provides an identification method of a silkworm silk fibroin solution for identifying the quality of the silk fibroin solution, including the following steps in sequence:

(1) adding the silk fibroin solution into an 8 M urea solution, incubating the resulting solution in a thermostatic water bath for a period of time, and centrifuging to collect the supernatant;

(2) treating the supernatant by column chromatography, wherein the eluant is a 4 M urea solution; and (3) identifying the eluted solution.

Preferably, the chromatographic column is also loaded with marker proteins, including conalbumin, ferritin and thyroglobulin.

5. In another aspect, the present invention provides a method of applying a freeze-dried powder on a pharmaceutical carrier after dissolution, i.e. a method of preparing silk fibroin microspheres with polyethylene glycol, including the following steps:

placing a silk fibroin solution of 1-30% by weight and a polyethylene glycol solution of 10-60% by weight under 4-60° C. for 30 min, and then uniformly mixing the silk fibroin solution and the polyethylene glycol solution in a certain ratio, and then incubating the resulting solution for a period of time, centrifuging and washing to prepare a suspension of silk fibroin microspheres.

Preferably, the polyethylene glycol has a molecular weight of 2000-20000.

Preferably, the polyethylene glycol has a molecular weight of 4000-20000.

Preferably, for the polyethylene glycol, a molecular weight of 4000, 6000 corresponds to a concentration of 30-60% by weight, a molecular weight of 10000 corresponds to a concentration of 20-50% by weight, and a molecular weight of 20000 corresponds to a concentration of 20-40% by weight.

Preferably, the silk fibroin solution has a dilution limit of 5-15% by weight.

Preferably, the temperature at which the silk fibroin solution and the polyethylene glycol solution are placed ranges from room temperature to 60° C.

Preferably, the volume ratio of the silk fibroin solution and the polyethylene glycol solution is 5:1-1:10.

Preferably, the volume ratio of the silk fibroin solution and the polyethylene glycol solution is 2:1-1:5.

Preferably, the incubation is performed at room temperature for 1-24 h.

Preferably, the silk fibroin solution is prepared in three procedures: (1) the degummed silk is infiltrated in a 9.3M LiBr solution and placed in an oven at 60° C. for 4 h to give a silk fibroin solution after dissolution; the silk fibroin solution is poured into a dialysis tube and dialyzed against deionized water for 3 d; after dialysis is completed, the silk fibroin solution is centrifuged to remove insoluble impurities, and then is poured into a dialysis tube and dialyzed against a 15 wt % polyethylene glycol solution having a molecular weight of 20000 for 24 h to obtain a concentrated silk fibroin solution; (2) the above freeze-dried powder is dissolved to a specified concentration; and (3) a silk fibroin solution is prepared by using the above improved method.

6. In a still other aspect, the present invention provides use of a freeze-dried powder in a controlled-release or sustained-release silk fibroin gel formulation for treating an inner ear disease. The controlled-release or sustained-release silk fibroin gel formulation for treating an inner ear disease of the present invention includes a formulation body which includes a gel-state carrier and a drug dispersed in or adsorbed to the carrier. The drug is for treating an inner ear disease, the carrier is a silk fibroin gel, the silk fibroin gel is prepared from a silk fibroin solution by induction gelling, and the silk fibroin solution is obtained by dissolving the freeze-dried powder.

Specifically, the induction gelling includes pH change, ultrasonic vibration, electrophoresis, blending with HRP (horseradish peroxidase)-$H_2O_2$ (hydrogen peroxide), and blending with low-molecular weight polyethylene glycol (PEG).

Preferably, the induction gelling is blending with low-molecular weight polyethylene glycol (PEG).

Specifically, the formulation body is prepared by mixing the drug in the form of aqueous solution or insoluble microspheres with the silk fibroin solution, followed induction gelling.

Specifically, the concentration of silk fibroin in the formulation body is 1-30%.

Preferably, the concentration of silk fibroin in the formulation body is 7.5-15%.

Specifically, the disease includes Meniere's Disease, sudden sensorineural hearing loss (SSNHL), Meniere's syndrome, sensorineural hearing loss, and autoimmune inner ear disease (AEID), and the drug includes one or more of dexamethasone, betamethasone, prednisolone, methylprednisolone, desoxycorticosterone, 11-desoxycorticosterone, 18-H-11-desoxycorticosterone, beclomethasone, triamcinolone acetonide, and chemical synthetic derivatives thereof.

In a still more other aspect, the present invention also provides a method of preparing the controlled-release or sustained-release silk fibroin gel formulation for treating an inner ear disease, including the following steps:

(1) mixing: the drug for treating an inner ear disease in the form of aqueous solution or insoluble microspheres is uniformly mixed with the silk fibroin solution to give a drug suspension; and (2) gelling: the drug suspension is prepared into the formulation body by induction gelling.

Preferably, the induction gelling includes pH change, ultrasonic vibration, electrophoresis, blending with HRP (horseradish peroxidase)-($H_2O_2$ hydrogen peroxide), and blending with low-molecular weight polyethylene glycol (PEG).

Preferably, some poorly water soluble drugs are dissolved in low-molecular weight polyethylene glycol (PEG), and the solution is further mixed with silk fibroin solution to induce gelling.

Preferably, the drug is also subjected to a coating treatment in order to uniformly blend water-insoluble drug particles into the silk fibroin solution in the mixing step, as well as to retard drug release. The coating treatment includes the following steps:

(a) suspending the drug particles in a low concentration of a silk fibroin solution, and performing ultrasonication for a period of time to disperse the agglomerated microspheres; and (b) centrifugating the resulting solution of step (a), and removing the supernatant removal, washing with water, and drying, to give the drug particles coated with a silk fibroin layer.

If it is desired to obtain the drug particles coated with multiple layers of silk fibroin coatings, the steps a-b are repeated.

The controlled-release or sustained-release silk fibroin gel formulation for treating an inner ear disease of the present invention is used in two ways: in-situ gelling and pre-gelling. The in-situ gelling and the pre-gelling are the same in the gelling manner, and different only in specific usage manner. In particular, for the pre-gelling, gelling is performed in vitro followed by injection or implantation into the inner ear, and for the in-situ gelling, a drug suspension is injected into the entire space of the round window niche and then a semi-solid gel of a suitable form is formed, thereby maximizing contact with the surface of the round window membrane; and the pre-gelling does not require a particular position of a patient, this is more convenient, but there is the disadvantage that at a high concentration, the injection is difficult to perform by using a thin needle.

By means of the above technical solutions, the present invention has the following advantages:

(1) In the preparation process of a freeze-dried powder of high molecular weight silk fibroin of the present invention, starting from control of the intermolecular interaction force of silk fibroin, by changing the pH value and ionic strength of the silk fibroin solution and in combination with high temperature and high pressure treatment, the silk fibroin is induced to form stable nanoparticles of about 50-300 nm, the tendency of further agglomeration of silk fibroin is inhibited, and thus a freeze-dried powder can be obtained by the basic freeze-drying procedure. Because high temperature and high pressure treatment (sterilization) has been performed before freeze-drying, the silk fibroin powder can be directly used in clinical treatment without further disinfection, thereby greatly simplifying the operation and saving the cost. The preparation process of the present invention is simple, and the resultant freeze-dried powder will not change the native molecular weight and random coil structure of silk fibroin, and can be rapidly dissolved into a high-concentration solution after adding water, for preparing various forms of biodegradable medical materials of silk fibroin. The freeze-dried powder can be stored and transported for a long time (more than one year) at room temperature, and this will greatly reduce waste of silk fibroin materials, improve the convenience and reliability in use, and promotes research & development and biomedical applications of silk fibroin biomaterials.

(2) The freeze-dried powder of high molecular weight silk fibroin of the present invention can maintain the random coil molecular structure of silk fibroin during freezing and drying, such that it does not convert to the β-sheet structure or the degree of conversion is controlled, and thus the intermolecular interaction, aggregation and crystallization of silk fibroin can be effectively prevented. The silk fibroin freeze-dried powder of the present invention can be rapidly and completely dissolved in water at high concentrations, and applied in various biomedical and clinical fields.

(3) The preparation of a silk fibroin solution using the improved method has the following advantages: (a) no strong acid or base is used, thereby avoiding substantial hydrolysis of silk fibroin and obtaining a high molecular weight of silk fibroin; (b) the gradient dialysis using a protein denaturant such as urea restores the secondary structure of silk fibroin, allows renaturation of the unfolded and denatured structure into the naive structure in solution that is dominated by α-helices and random coils, and facilitates the processing of silk fibroin-based biomaterials, and in processing silk fibroin-based biomaterials, particularly pharmaceutical carrier materials, the pre-formed β-sheet structure is disadvantageous for drug encapsulation and conversion of material forms (for example, formation of microspheres of uniform size, the time needed to form a gel); (c) the silk dissolution without the use of a 9.3 M aqueous lithium bromide solution reduces the preparation cost of silk fibroin, improves the product safety, and facilitates the research and industrialization of silk fibroin; (d) the silk fibroin solution obtained by the present invention has a clear appearance, a molecular weight close to that of native fibroin molecules, and good dispersibility of fibroin molecules in the solution; (e) the ternary solution of calcium chloride, water and ethanol at a molar ratio of 1:8:2 is inexpensive, and not disruptive to the column chromatography system, and can be used in column chromatography after the viscosity is reduced, this provides the possibility of preparing a silk fibroin solution by using column chromatography; and (f) the protein denaturant, particularly urea, is inexpensive, this facilitates the research and industrialization of silk fibroin.

(4) The pharmaceutical adjuvant polyethylene glycol is selected to blend with the silk fibroin solution for preparing silk fibroin hydrogel and microspheres. The preparation process does not require complex devices, the operation process is simple, easy and takes less time and cost, and no organic solvent is added. The prepared silk fibroin hydrogel and microspheres have high bio-safety and can be directly used clinically.

(5) As a controlled-release or sustained-release formulation, the drug of the present invention can be used for treating an inner ear disease. With an injectable silk fibroin gel as a pharmaceutical carrier, the gelling time of a silk fibroin-PEG solution is highly controllable (Wang X, Partlow B, Liu J, et al. Injectable silk-polyethylene glycol hydrogels. Acta Biomater. 2015; 15(12):51-61); the preparation scheme with in-situ gelling can achieve the standard of zero order release, the drug-release time can reach at least 10 days, and there is no detrimental effect on hearing. In addition, as a pharmaceutical carrier, the silk fibroin-PEG gel is safe and non-toxic, and is degraded slowly. It is indicated that the injectable silk fibroin-PEG gel is a safe and effective pharmaceutical carrier, and can be used in a sustained-release drug for treating an inner ear disease.

Detailed Description of the Preferred Embodiments

Figure 1:
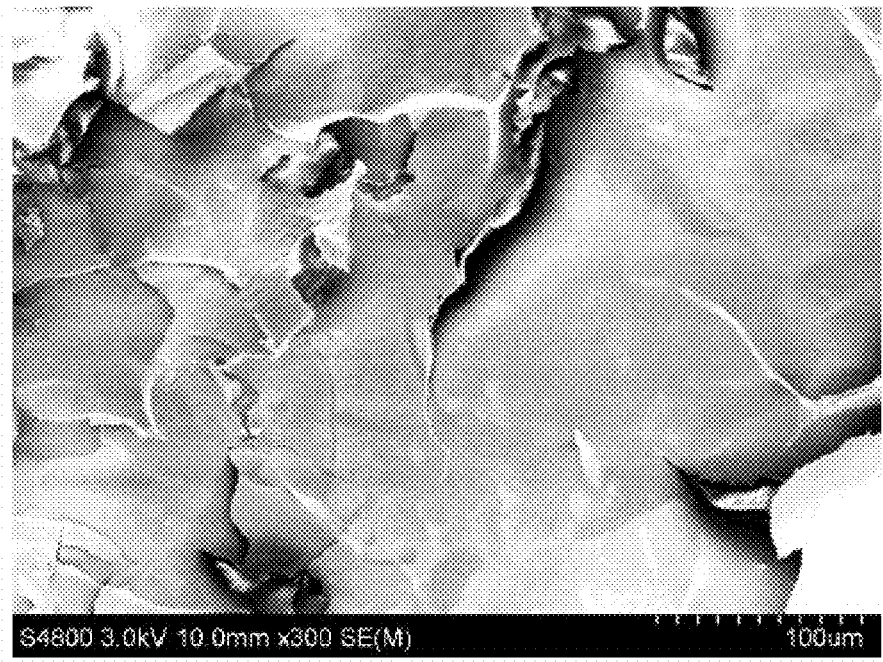
FIG. 1 is an electron micrograph of a sheet-like structure after freeze-drying of an original silk fibroin solution without treatment according to the present invention.

The invention will be further illustrated in more detail with reference to accompanying drawings. It is noted that, the following embodiments are intended for purposes of illustration only and are not intended to limit the scope of the invention.

Example 1

The present invention provides a preparation process of a freeze-dried powder of high molecular weight silk fibroin, and the process includes the following steps.

Silk is boiled in an amount of a sodium carbonate solution for a period of time, and soaked and washed with clear water to give degummed silk, and after air drying, a suitable amount of the degummed silk is dissolved in a lithium bromide solution. After the degummed silk is completely dissolved, the resulting solution is dialyzed in a dialysis tube for two days, such that lithium bromide diffuses through the dialysis tube and silk fibroin is retained in the dialysis tube. Following dialysis, the silk fibroin solution is centrifuged, and the supernatant is taken as a silk fibroin solution. After the concentration of the solution is determined, it is mixed with a phosphate buffer solution to prepare a 3% w/v silk fibroin solution. The solution is treated by high temperature (121° C.) and high pressure (0.1 Mpa) for 20 min. A volume of the solution is transferred into a glass bottle and frozen overnight. After freeze-drying for a period of time, the freeze-dried powder of high molecular weight silk fibroin of the present invention is obtained.

Specific experimental steps are as follows:

S1: silk degumming: 30 g silk is boiled in 25.44 g sodium carbonate/12 L deionized water for 0.5 h. Silk is continuously stirred during the boiling such that it is dispersed to prevent from being bonded together, and after the boiling, degummed silk is removed, washed with deionized water three times to remove silk sericin, leaving silk fibroin, and the silk fibroin is dried on a super-clean bench overnight;

S2: dissolution with lithium bromide: 10 g of the degummed silk is placed in 40 ml of a 9.3 M lithium bromide solution, stirred with a glass rod such that the degummed silk is sufficiently impregnated, and heated in an oven at 60° C. for 4 h;

S3: dialysis: dialysis is performed using a Pierce dialysis device having a molecular weight cut-off of 3500-10000 Daltons or a common dialysis tube for 36 h, water is changed at 3, 6, 12, 18, 24, 30, and 36 h from the dialysis, respectively, to remove the lithium bromide in the solution, leaving silk fibroin in the dialysis tube;

S4: centrifugation: the silk fibroin solution in the dialysis tube is transferred into a centrifuge container and centrifuged at 9000 rmp for 20 min at 4° C., the precipitate is discarded, and the supernatant solution is taken as the subject silk fibroin solution;

S5: concentration determination: an amount of the silk fibroin solution is dried over 3 h at 60° C., and the resulting silk fibroin membrane is weighed to obtain the concentration of the silk fibroin solution (w/v);

S6: high temperature and high pressure treatment: the silk fibroin solution is diluted with ultrapure water to a concentration of 6%, and the silk fibroin solution at a concentration of 6% is uniformly mixed with a 10 mM PB buffer having a pH=7.4 in a volume ratio of 1:1, so that the final concentration of the silk fibroin solution is 3% (w/v) and the final concentration of the PB buffer is 5 mM after mixing, and then the solution is transferred to a glass container and is subjected to high temperature and high pressure treatment at 121° C. and 0.1 Mpa for 20 min; and S7: freeze-drying: 10 ml of the treated solution is thoroughly frozen at a temperature of below −20° C. in a sterile, 15 ml glass bottle, and then evacuated in a lyophilizer over 48 h to induce ice sublimation, giving the freeze-dried powder of high molecular weight silk fibroin.

Lithium bromide in S2 can be replaced with another compound, such as a calcium chloride/ethanol/water ternary mixture at a molar ratio of 1:2:8.

The dialysis in S3 can be replaced with desalting column chromatography to remove lithium bromide or other salt ions. If desalting column chromatography is used in S3, then S4 can be omitted.

The PB buffer in S6 can be replaced with another buffer capable of maintaining the stable pH, such as tris buffer, sodium acetate buffer, ammonium chloride buffer.

The concentration and the volume ratio of the silk fibroin solution and the PB buffer in S6 can vary, but in the mixture, the final concentration of the silk fibroin solution is not greater than 3% (w/v) and the final concentration of the PB buffer is not less than 5 mM.

TABLE 1

Effects of high molecular weight silk fibroin powders at different conditions

| | Final concentration after dilution | Final concentration of PB buffer | High pressure sterilization | Solubility of freeze-dried powder |
|---|---|---|---|---|
| Silk fibroin solution | 3% | 5 mM | Yes | good solubility |
| Silk fibroin solution | 3% | 5 mM | No | insoluble |
| Silk fibroin solution | 3% | No | Yes | with insoluble particles |
| Silk fibroin solution | 3% | No | No | insoluble |
| Silk fibroin solution | 4% | 5 mM | Yes | soluble, but lower than that for 3% |
| Silk fibroin solution | 4% | 5 mM | No | insoluble |
| Silk fibroin solution | 4% | No | Yes | insoluble |
| Silk fibroin solution | 4% | No | No | insoluble |
| Silk fibroin solution | 5% | 5 mM | Yes | insoluble |
| Silk fibroin solution | 5% | 5 mM | No | insoluble |
| Silk fibroin solution | 5% | No | Yes | insoluble |
| Silk fibroin solution | 5% | No | No | insoluble |

For the freeze-dried powders prepared by the above methods, they are stored in such a manner that: sealed glass containers charged with the freeze-dried powders are placed at room temperature and stored protected from light. They are used in such a manner that: the freeze-dried powder is dissolved and an amount of purified water is added, the resulting solution is slowly rotated to uniformly mix until all the dried powder contact water, and then allowed to stand for 5-10 min until it is completely dissolved into a clear silk fibroin solution, wherein slow stirring may be performed to promote the dissolution.

Figure 2:
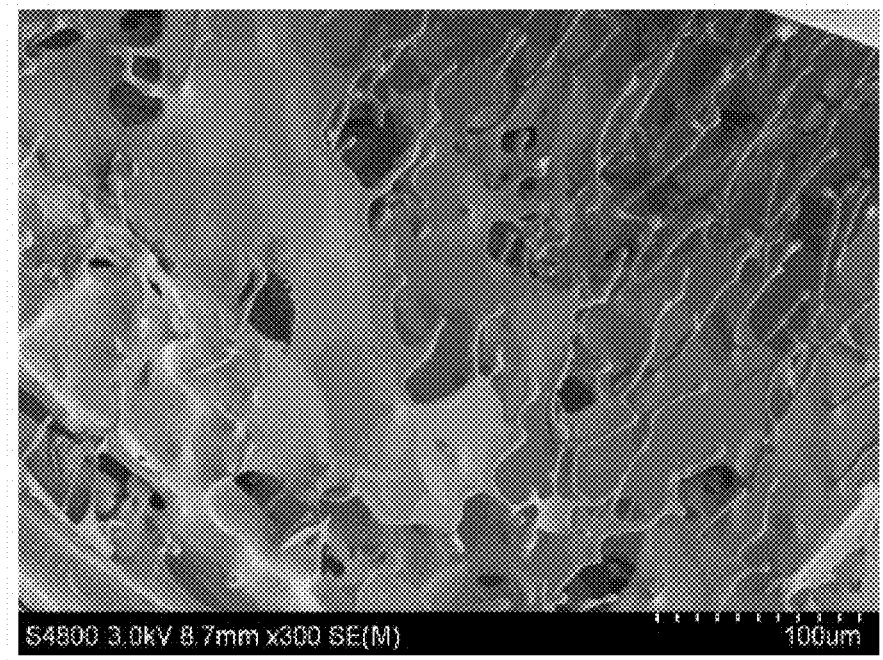
FIG. 2 is a scanning electron micrograph of a freeze-dried powder of high molecular weight silk fibroin according to the present invention.

Microscopic topography of freeze-dried powder: an original silk fibroin solution is freeze-dried to form a powder of a sheet-like structure, and the freeze-dried powder has a dense structure and is insoluble in water. After adjustment of the pH value and high temperature sterilization, the prepared freeze-dried powder of high molecular weight silk fibroin has a porous structure, and can be rapidly dissolved in water, as shown in FIG. 1 and FIG. 2.

Figure 3:
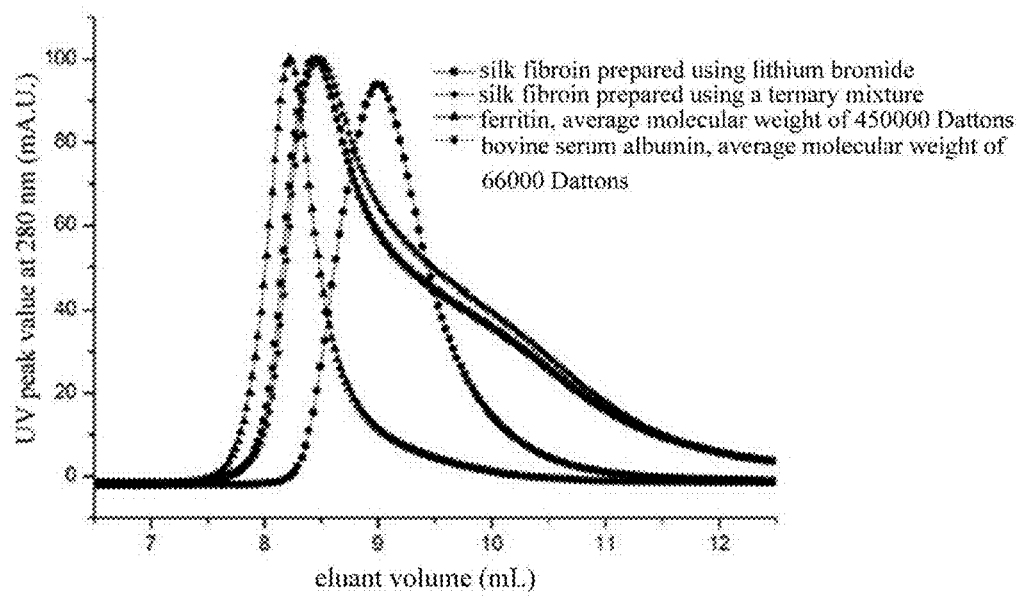
FIG. 3 is a graph showing the results of molecular weight analysis of silk fibroin prepared by different methods of the present invention.

Molecular weight of freeze-dried powder: for the freeze-dried powder of high molecular weight silk fibroin made from silk fibroin solutions that are prepared by two different methods using Lithium bromide and calcium chloride-containing ternary solution, the molecular weight does not show significant difference and is closed to that of ferritin, which is much higher than that of bovine serum albumin (BSA) of molecular weight 66000 Daltons, as shown in FIG. 3.

Figure 4:
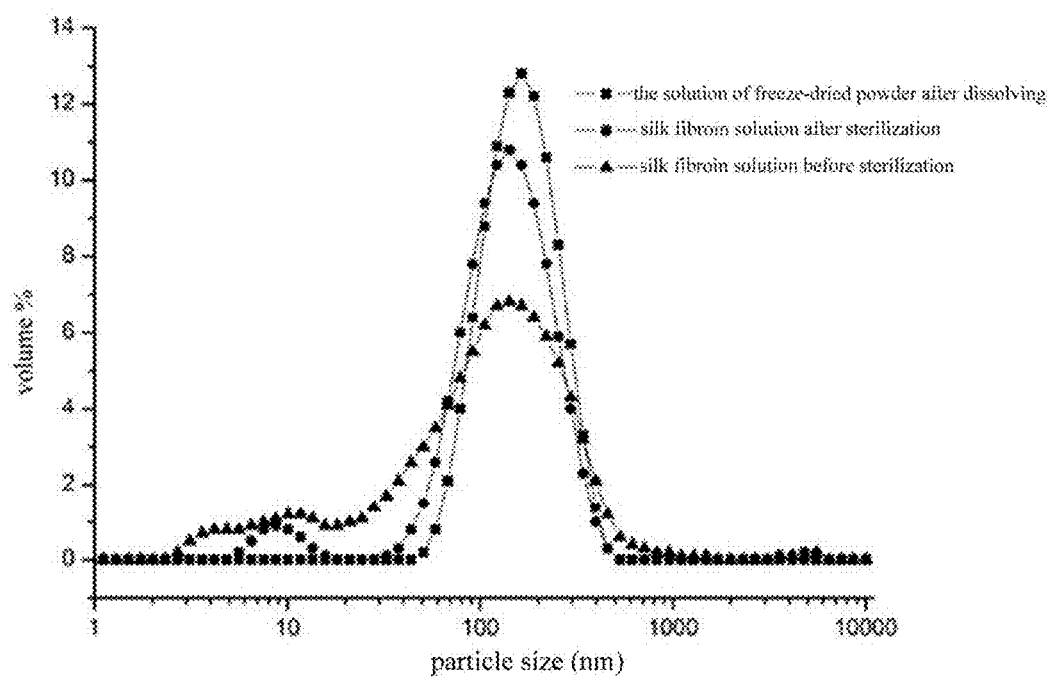
FIG. 4 is a graph showing changes in particle size during the fabrication of a freeze-dried powder of high molecular weight silk fibroin according to the present invention.

Particle size of freeze-dried powder: high temperature and high pressure sterilization can induce conversion of silk fibroin from a complex molecular structure such as single molecule, multimer and nanoparticles into stable nanoparticles of about 50-300 nm, reducing the intermolecular interaction force and inhibiting further agglomeration of silk fibroin. Thus, the freeze-dried powder is present in a solution as particles of 50-300 nm after hydration, and the size of the particles remains unchanged before and after high temperature and high pressure treatment and after dissolution of the freeze-dried powder. The number of nanoparticles increases after high temperature and high pressure treatment though. As shown in FIG. 4.

Figure 5:
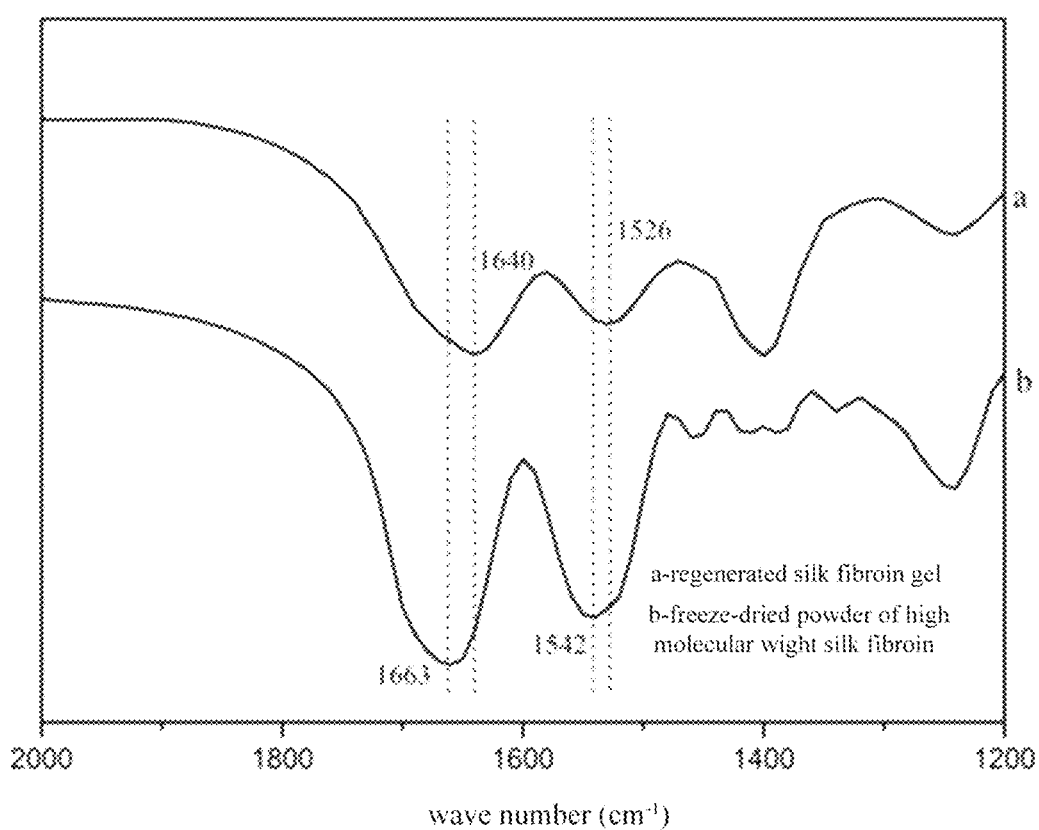
FIG. 5 shows the Fourier-Transform Infra-Red spectrum of a regenerated silk fibroin solution after gelling and a freeze-dried powder of high molecular weight silk fibroin according to the present invention.
Figure 6:
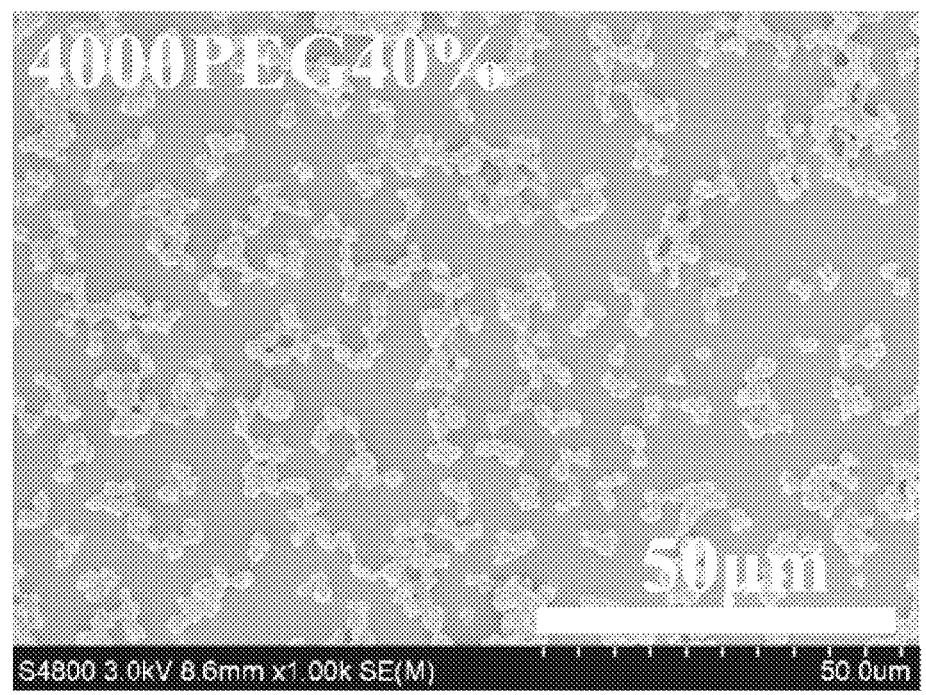
FIG. 6 is a scanning electron micrograph of silk fibroin microspheres prepared by blending a PEG solution of a molecular weight of 4000 and a concentration of 40 wt % with an 8 wt % silk fibroin solution.
Figure 7:
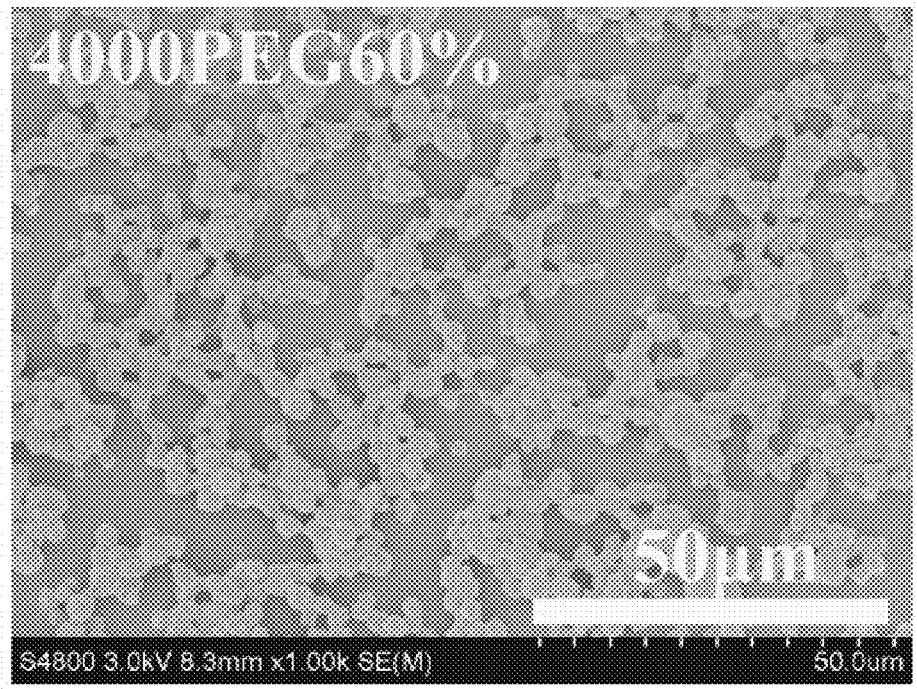
FIG. 7 is a scanning electron micrograph of silk fibroin microspheres prepared by blending a PEG solution of a molecular weight of 4000 and a concentration of 60 wt % with an 8 wt % silk fibroin solution.
Figure 8:
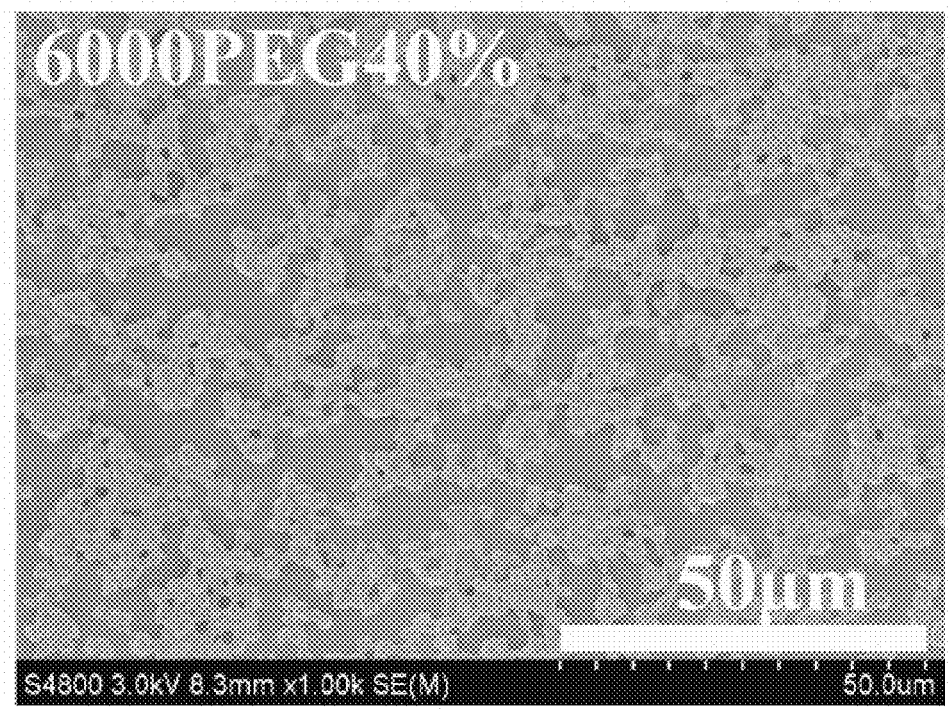
FIG. 8 is a scanning electron micrograph of silk fibroin microspheres prepared by blending a PEG solution of a molecular weight of 6000 and a concentration of 40 wt % with an 8 wt % silk fibroin solution.
Figure 9:
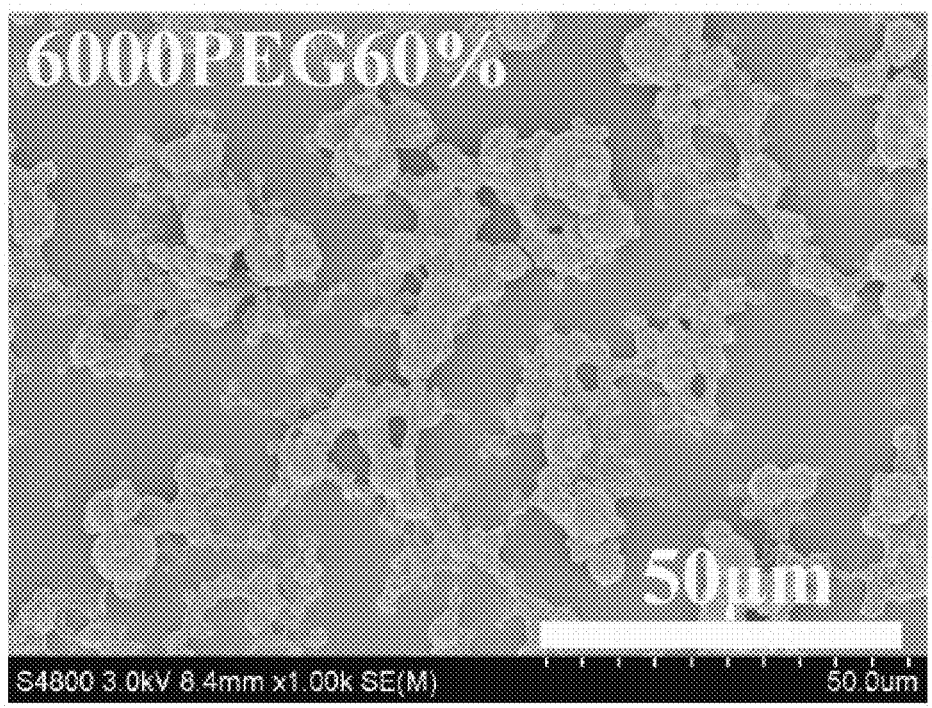
FIG. 9 is a scanning electron micrograph of silk fibroin microspheres prepared by blending a PEG solution of a molecular weight of 6000 and a concentration of 60 wt % with an 8 wt % silk fibroin solution.
Figure 10:
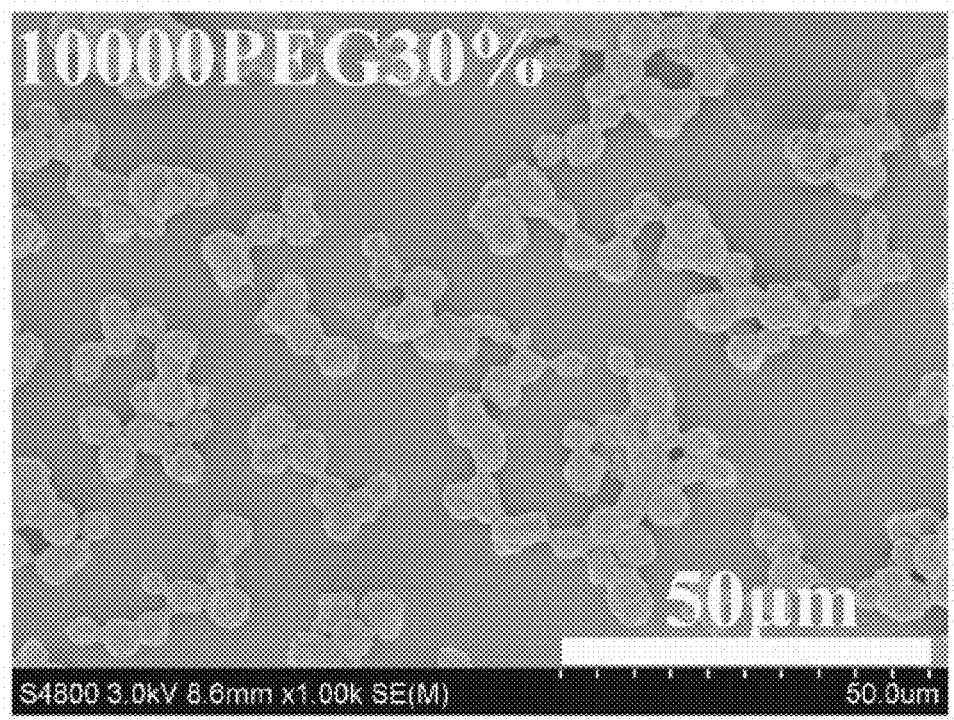
FIG. 10 is a scanning electron micrograph of silk fibroin microspheres prepared by blending a PEG solution of a molecular weight of 10000 and a concentration of 30 wt % with an 8 wt % silk fibroin solution.
Figure 11:
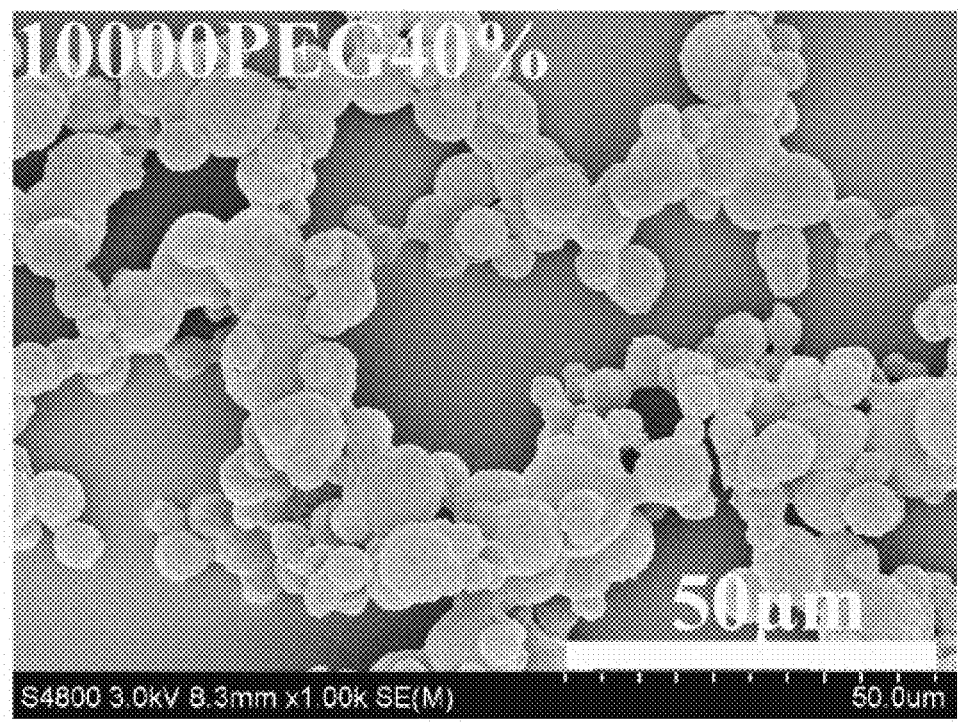
FIG. 11 is a scanning electron micrograph of silk fibroin microspheres prepared by blending a PEG solution of a molecular weight of 10000 and a concentration of 40 wt % with an 8 wt % silk fibroin solution.
Figure 12:
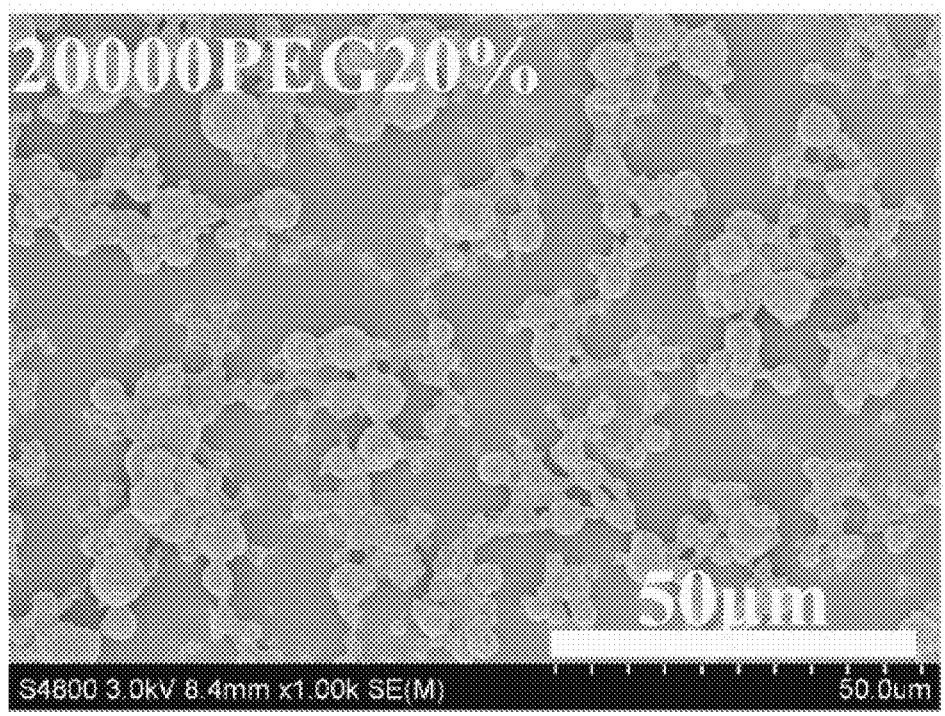
FIG. 12 is a scanning electron micrograph of silk fibroin microspheres prepared by blending a PEG solution of a molecular weight of 20000 and a concentration of 20 wt % with an 8 wt % silk fibroin solution.
Figure 13:
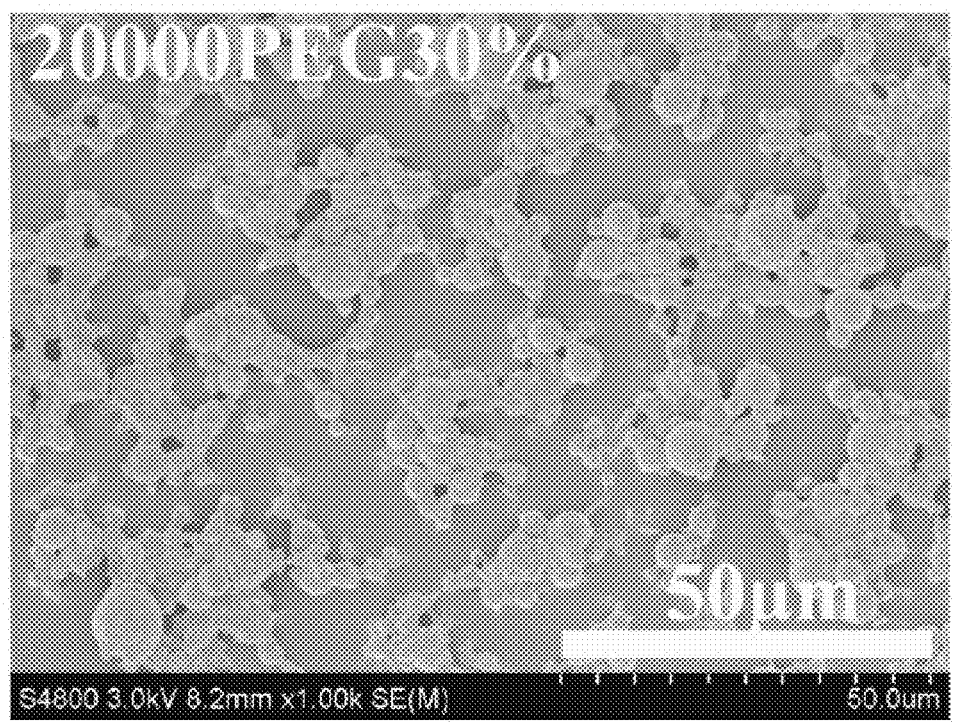
FIG. 13 is a scanning electron micrograph of silk fibroin microspheres prepared by blending a PEG solution of a molecular weight of 20000 and a concentration of 30 wt % with an 8 wt % silk fibroin solution.
Figure 14:
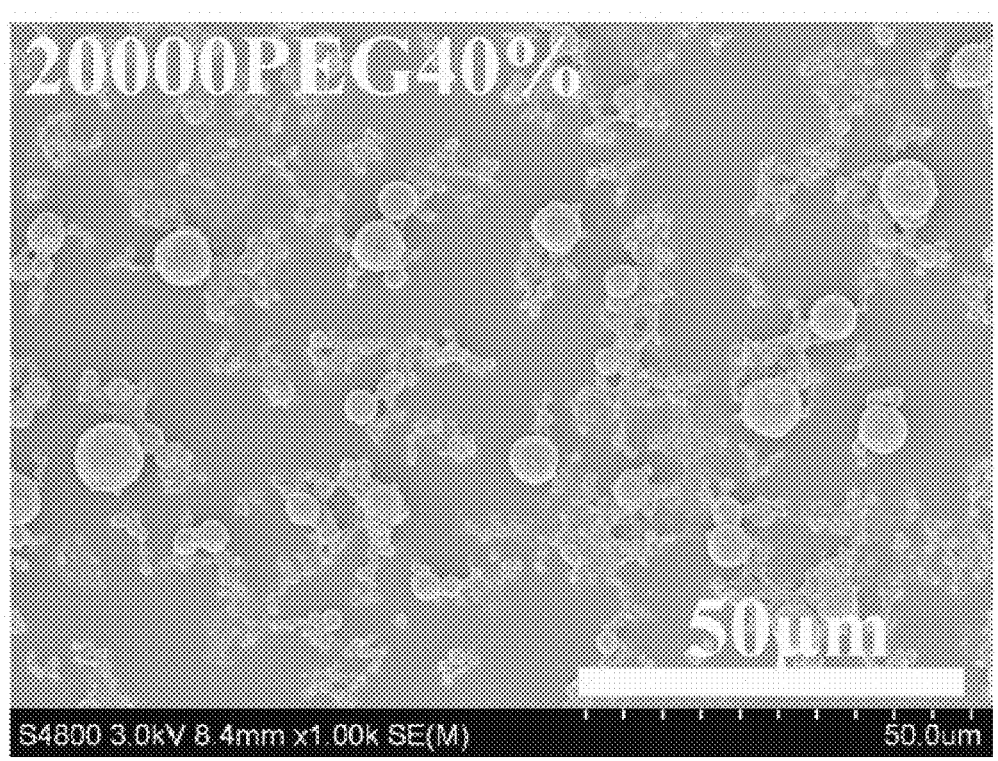
FIG. 14 is a scanning electron micrograph of silk fibroin microspheres prepared by blending a PEG solution of a molecular weight of 20000 and a concentration of 40 wt % with an 8 wt % silk fibroin solution.

Structure of freeze-dried powder: in the infrared absorption spectrum of silk fibroin, characteristic absorption peaks of the silk I structure appear at near 1650 cm-1, 1665 cm-1 (amide I), 1545 cm-1 (amide II), 1240 cm-1 (amide III), and 669 cm-1 (amide V), respectively. Characteristic absorption peaks of the silk II structure appear at 1625-1640 cm-1 (amide I), 1515-1525 cm-1 (amide II), 1265 cm-1 (amide III), and 696 cm-1 (amide V), respectively. Characteristic infrared absorption peaks of a gel made from the dissolved high molecular weight silk fibroin powder mainly appear at 1640 cm-1 and 1526 cm-1, i.e. the β-sheet structure, while characteristic infrared absorption peaks of the high molecular weight silk fibroin powder mainly appear at 1663 cm-1 and 1542 cm-1, i.e. the α-helical-shaped and random coil structure. Therefore, the structure of the freeze-dried powder is dominated by random coils and α-helices, as shown in FIG. 5.

Gelling properties after dissolution of freeze-dried powder: the silk fibroin gel has the advantages of good biocompatibility and slow degradation, and is used in the fields such as prevention and treatment of skin diseases, postoperative hemostasis and adhesion prevention, and sustained release of drugs. The gelling of silk fibroin is an important property of silk fibroin. A silk fibroin solution of 3 to 30% (w/v) is thoroughly mixed with low molecular weight liquid polyethylene glycol 300 or 400 to give a blend and the blend is gelled after a period of time. With different concentrations of silk fibroin and polyethylene glycol, the gelling time can vary. The volume ratio of the polyethylene glycol and silk fibroin solutions is 1:1. The gelling time is an important indicator in analysis of properties of the silk fibroin solution. The gelling of the silk fibroin solution is determined by inverting a test tube to observe the flow of silk fibroin. By respectively mixing the original silk fibroin solution and the regenerated silk fibroin solution with polyethylene glycol 400 to form a gel, it is concluded that there is no significant difference in gelling time between the regenerated silk fibroin solution and the original silk fibroin solution, indicating that the regenerated silk fibroin solution has good gelling properties, as shown in Table 2. The gelling times obtained by replacing polyethylene glycol 400 with polyethylene glycol 300 are relatively long, but have the same tendency, that is, there is no significant difference in gelling time between the regenerated silk fibroin solution and the original silk fibroin solution.

TABLE 2

Gelling time of original/regenerated silk fibroin solutions after mixing with polyethylene glycol 400 at different concentrations respectively

| Concentration of silk fibroin solution | | Concentration of PEG 400 | | |
|---|---|---|---|---|
| | | 75%(w/w) | 80%(w/w) | 85%(w/w) |
| Concentration of original silk fibroin solution | 7.5%(w/v) | 112 min gelling | 44 min gelling | 19 min gelling |
| | 15%(w/v) | 45 min gelling | 28 min gelling | 10 min gelling |
| | 30%(w/v) | 21 min gelling | 16 min gelling | 5 min gelling |
| Concentration of regenerated silk fibroin solution | 7.5%(w/v) | 128 min gelling | 48 min gelling | 22 min gelling |
| | 15%(w/v) | 47 min gelling | 28 min gelling | 14 min gelling |
| | 30%(w/v) | 26 min gelling | 17 min gelling | 7 min gelling |

Example 2

Silk fibroin biomaterial has excellent physical and chemical properties, is non-toxic and non-irritating, has good biocompatibility, is biodegradable, and meets the requirements of biomaterials to a large degree. Also, silk fibroin has outstanding processability, can be prepared into films, gels, microspheres, porous scaffolds etc., and can be processed into a gel state or a microsphere state by different processes to meet different drug loading requirements. A method of preparing a silk fibroin gel or silk fibroin microspheres with polyethylene glycol is provided in this embodiment.

2.1 Preparation of a Silk Fibroin Solution 2.1.1 25 g the degummed silk is weighed, dipped in 100 mL of a 9.3M LiBr solution, and placed in an oven at 60° C. for 4 h, with stirring once every 1 h to be completely dissolved, giving a 20% (w/v) silk fibroin solution. The silk fibroin solution is poured into a Slide-α-lyzer dialysis tube having a molecular weight cut-off of 3500. The dialysis cassette is placed into a dialysis bath containing deionized water for three days, during which water is changed 10 times. After dialysis is completed, the silk fibroin solution is centrifuged at 9000 rpm/min for 20 min at 4° C. to remove insoluble impurities. Determination of the concentration of the silk fibroin solution is performed by weighing an amount of the silk fibroin solution, drying in an oven at 60° C., and then weighing and calculating a ratio of the two values to give the concentration value (wt %). Generally, the concentration of the silk fibroin solution obtained is about 7 wt %. The concentration process of the silk fibroin solution is performed by transferring 100 mL of the prepared silk fibroin solution into a new Slide-α-lyzer dialysis tube, placing the dialysis tube into 800 mL of a 15 wt % polyethylene glycol solution of a molecular weight of 20000 for 24 h of continuous dialysis to obtain a concentrated silk fibroin solution of about 30 wt %, which is stored in a refrigerator at 4° C.

2.1.2 The silk fibroin solution described in this embodiment may be prepared by the method above, or the freeze-dried powder obtained in the example 1 may be dissolved to give the 30 wt % concentrated silk fibroin solution.

2.2 Preparation of a Polyethylene Glycol-Silk Fibroin Blend 2.2.1 The 30 wt % silk fibroin solution above is diluted to 1%-5 wt %;

Polyethylene glycol (PEG) solutions of different molecular weights are formulated at different concentrations: the concentration is 40-100 wt % for PEG of molecular weight less than 1000; the concentration is 10-60 wt % for PEG of molecular weight 1000-6000; the concentration is 10-50 wt % for molecular weight 10000; and the concentration is 10-40 wt % for molecular weight 20000;

Equal volumes of 1-5 wt % silk fibroin solutions are added into equal volumes of polyethylene glycol solutions of different molecular weights and concentrations, respectively, and gently pipetted up and down such that the blends are mixed uniformly;

The polyethylene glycol-silk fibroin blends are incubated at room temperature for 30 min;

The state of the blends after incubation are observed and recorded.

2.2.2 The 30 wt % silk fibroin solution above is diluted to 6-30 wt %;

Polyethylene glycol of different molecular weights is formulated at different concentrations: the concentration is 10-60 wt % for PEG of molecular weight 2000-6000; the concentration is 10-50 wt % for molecular weight 10000; and the concentration is 10-40 wt % for molecular weight 20000;

Equal volumes of 6-30 wt % silk fibroin solutions are added into equal volumes of polyethylene glycol solutions of different molecular weights and concentrations, respectively, and gently pipetted up and down such that the blends are mixed uniformly;

The polyethylene glycol-silk fibroin blends are incubated at room temperature for 30 min;

The state of the blends after incubation are observed and recorded.

The experimental results of 2.2.1 and 2.2.2 are summarized in Table 3. It can be seen from the recorded data that, polyethylene glycol of high molecular weight is easily blended with silk fibroin solutions to form particles; the molecular weight and concentration of polyethylene glycol and the concentration of silk fibroin solutions are the factors directly influencing the formation of particles.

TABLE 3

State table after blending silk fibroin with polyethylene glycol solutions for 30 min

| Molecular weight of PEG (D) | Concentration of PEG (wt %) | Concentration of Silk fibroin (wt %) | Blending state after 30 min |
|---|---|---|---|
| 200 | 100 | 1-5 | 1 wt % solution, 2-5 wt % gelling |
|  | 50 | 1-5 | 1-4 wt % solution, 5 wt % gelling |
|  | 45 | 1-5 |  |
|  | 40 | 1-5 |  |
|  | 100 | 1-5 | 1-5 wt % gelling |
| 300 | 55 | 1-5 | 1-2 wt % solution, 3-5 wt % gelling |
|  | 50 | 1-5 | 1-3 wt % solution, 4-5 wt % gelling |
| 300 | 45 | 1-5 |  |
| 400 | 100 | 1-5 | 1-5 wt % gelling |
|  | 55 | 1-5 | 1 wt % solution, 2-5 wt % gelling |
|  | 50 | 1-5 |  |
|  | 45 | 1-5 |  |
| 600 | 100 | 1-5 | 1-5 wt % gelling |
|  | 60 | 1-5 | 1-2 wt % solution, 3-5 wt % gelling |
|  | 55 | 1-5 | 1-3 wt % solution, 4-5 wt % gelling |
|  | 50 | 1-5 | 1-5 wt % solution |
| 1000 | 60 | 1-5 | 1 wt % solution, 2-5 wt % gelling |
|  | 55 | 1-5 | 1-2 wt % solution, 3-5 wt % gelling |
|  | 10 | 1-5 | 1-5 wt % solution |
| 1500 | 60 | 1-5 | 1 wt % solution, 2-5 wt % gelling |
|  | 55 | 1-5 | 1-2 wt % solution, 3-5 wt % gelling |
|  | 10 | 1-5 | 1-3 wt % solution, 4-5 wt % gelling |
| 2000 | 60 | 6-30 | 1 wt % solution, 2-30 wt % gelling |
|  | 50 | 6-30 | 1-2 wt % solution, 3-30 wt % gelling |
|  | 40 | 6-30 | 1-2 wt % solution, 3-30 wt % particles |
|  | 10 | 6-30 | 1-30 wt % solution |
| 4000 | 60 | 6-30 | 1-3 wt % solution, 4-30 wt % particles |
|  | 40 | 6-30 | 1-4 wt % solution, 5-30 wt % particles |
|  | 10 | 6-30 | 1-30 wt % solution |
| 6000 | 60 | 6-30 | 1-3 wt % solution, 4-30 wt % particles |
|  | 40 | 6-30 | 1-3 wt % solution, 4-30 wt % particles |
|  | 10 | 6-30 | 1-30 wt % solution |
| 10000 | 50 | 6-30 | 1-2 wt % solution, 3-30 wt % particles |
|  | 25 | 6-30 | 1-3 wt % solution, 4-30 wt % particles |
|  | 10 | 6-30 | 1-4 wt % solution, 5-30 wt % particles |
| 20000 | 40 | 6-30 | 1-2 wt % solution, 3-30 wt % particles |
|  | 20 | 6-30 | 1-3 wt % solution, 4-30 wt % particles |
|  | 10 | 6-30 | 1-30 wt % solution |

2.3 Preparation of Silk Fibroin Microspheres

A polyethylene glycol solution of molecular weight 4000 is formulated at a concentration of 40 wt % and 60 wt %, a polyethylene glycol solution of molecular weight 6000 is at a concentration of 40 wt % and 60 wt %, a polyethylene glycol solution of molecular weight 10000 is at a concentration of 30 wt %, 40 wt % and 50 wt %, and a polyethylene glycol solution of molecular weight 20000 is at a concentration of 20 wt %, 30 wt % and 40 wt %, respectively;

The 30 wt % silk fibroin solution above is diluted to 8 wt %, and this solution is added into equal volumes of the polyethylene glycol solutions of the concentrations and molecular weights above;

The polyethylene glycol-silk fibroin blends are incubated at room temperature for 12 h;

After incubation is completed, a centrifuge tube is placed in a centrifuge for centrifugation under conditions: room temperature, 25° C., 10 min, 12000 rpm/min;

Washing is performed by adding deionized water, the supernatant is removed, and the centrifugation and washing operations are repeated three times;

A suspension of silk fibroin microspheres is formulated with deionized water, placed in a refrigerator at 4° C. or stored after vacuum freeze drying.

Refer to FIGS. 6 to 14, which are scanning electron micrographs of silk fibroin microspheres prepared in this example. It can be seen from the figures that, the silk fibroin microspheres obtained after the PEG solution of a molecular weight of 10000 and a concentration of 40 wt % is blended with the 8 wt % silk fibroin solution have a larger particle size.

2.4 Detection of Particle Size of Silk Fibroin Microspheres

The suspensions of silk fibroin microspheres in 2.3 are taken and transferred into disposable cuvettes, respectively;

The particle size of samples of silk fibroin microspheres in each group is tested with a laser particle size analyzer for three times per group, and an average is calculated.

Figure 15:
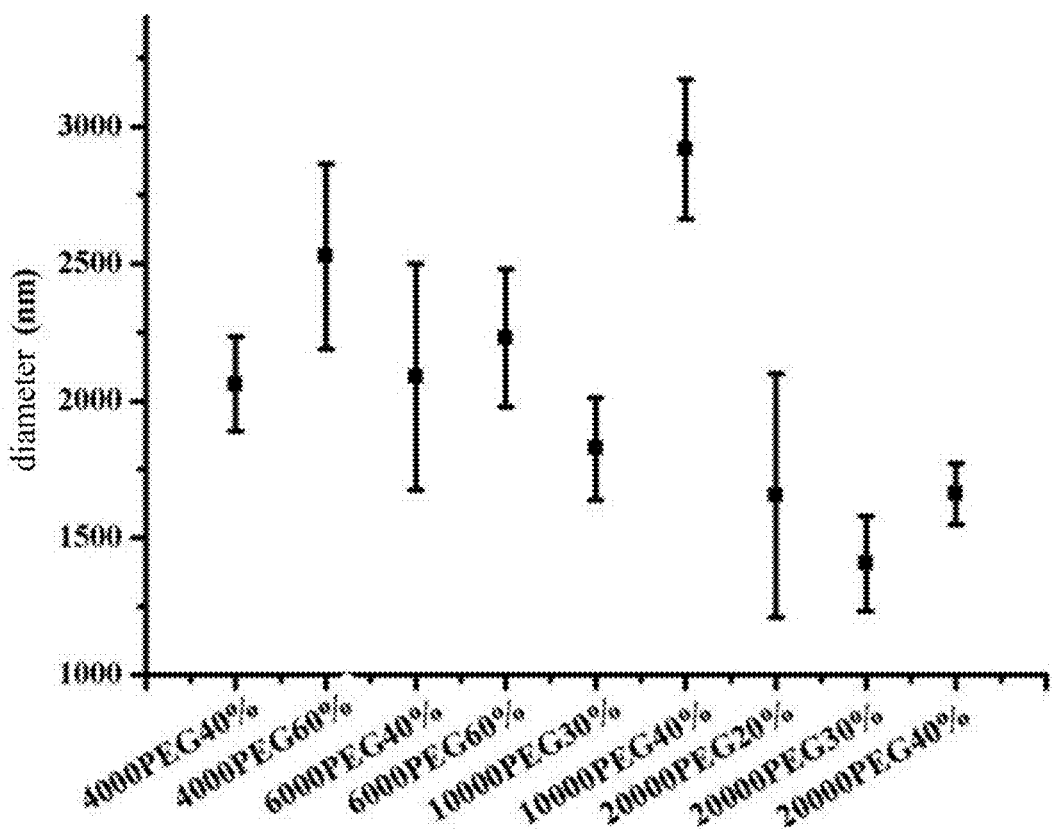
FIG. 15 is a diagram showing particle size distribution of silk fibroin microspheres prepared by blending a PEG solution of various molecular weights and concentrations with an 8 wt % silk fibroin solution.

Refer to FIG. 15, which is a diagram showing particle size distribution of silk fibroin microspheres in this example. It can be seen from the figure that, the particles of silk fibroin microspheres obtained after the PEG solution of a molecular weight of 10000 and a concentration of 40 wt % is blended with the 8 wt % silk fibroin solution have a larger particle size and a narrower particle size distribution.

2.5 Preparation of Silk Fibroin Microspheres 2.5.1 A polyethylene glycol solution of a molecular weight of 10000 and a concentration of 50 wt % is formulated;

The 30 wt % silk fibroin solution above is diluted to 5 wt % and 9 wt %;

The two solutions above are taken and mixed in equal volumes, and incubated at room temperature for 2 h;

After incubation is completed, a centrifuge tube is placed in a centrifuge for centrifugation under conditions: room temperature, 10 min, 12000 rpm/min;

Washing is performed by adding deionized water, the supernatant is removed, and the centrifugation and washing operations are repeated three times;

A suspension of silk fibroin microspheres is formulated with deionized water, placed in a refrigerator at 4° C. or stored after vacuum freeze drying.

Figure 16:
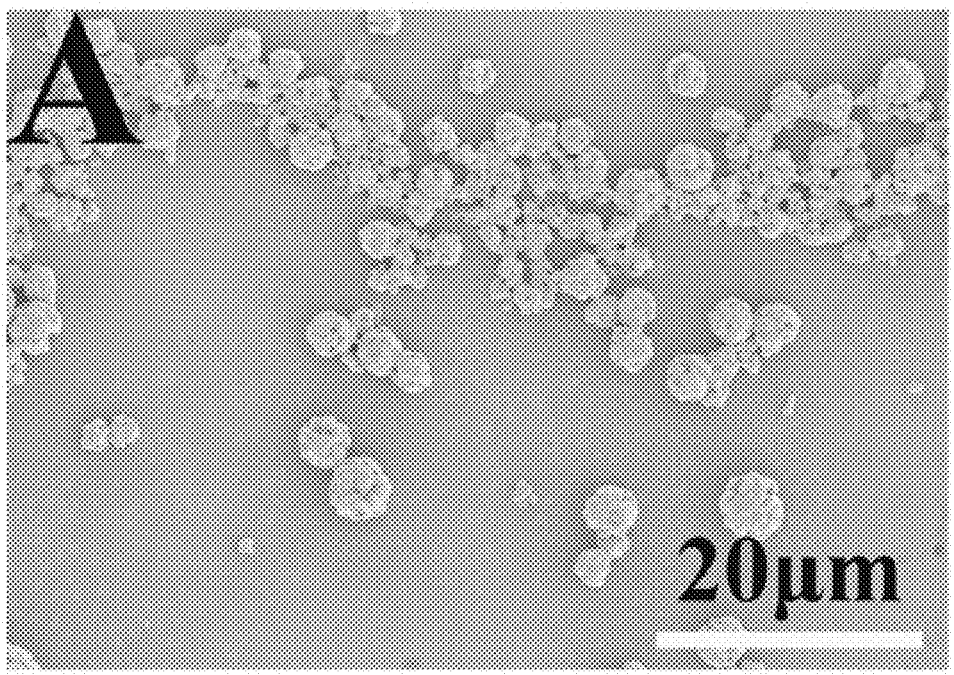
FIG. 16 is a scanning electron micrograph of silk fibroin microspheres prepared by blending a PEG solution of a molecular weight of 10000 and a concentration of 50 wt % with a 5 wt % silk fibroin solution.
Figure 17:
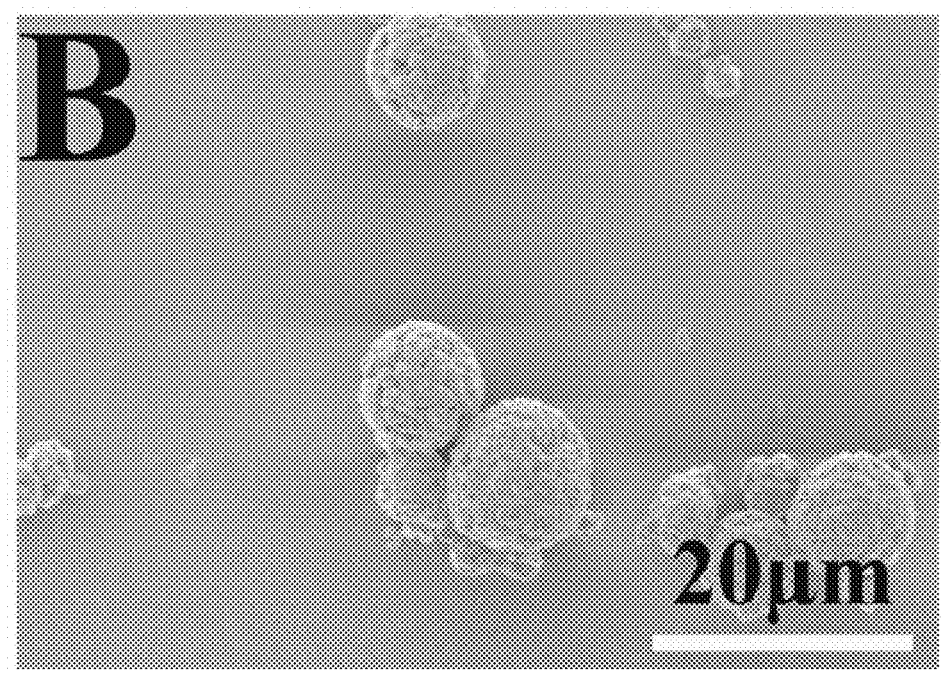
FIG. 17 is a scanning electron micrograph of silk fibroin microspheres prepared by blending a PEG solution of a molecular weight of 10000 and a concentration of 50 wt % with a 9 wt % silk fibroin solution.

Refer to FIGS. 16 to 17, which are scanning electron micrographs of silk fibroin microspheres prepared in this example. It can be seen from the figures that, the particle size of silk fibroin microspheres is affected by the concentration of the silk fibroin solution, and the particle size of silk fibroin microspheres prepared from the 9 wt % silk fibroin solution is larger than the particle size of silk fibroin microspheres prepared from the 5 wt % silk fibroin solution.

2.5.2 A polyethylene glycol solution of a molecular weight of 4000 and a concentration of 60 wt % is formulated;

The 30 wt % silk fibroin solution above is diluted to 5 wt %;

The two solutions above are placed in an oven at 60° C. for 30 min;

The two solutions above are taken and mixed in a 1/1 ratio (polyethylene glycol/silk fibroin) and incubated at room temperature for 1 h;

After incubation is completed, a centrifuge tube is placed in a centrifuge for centrifugation under conditions: room temperature, 10 min, 12000 rpm/min;

Washing is performed by adding deionized water, the supernatant is removed, and the centrifugation and washing operations are repeated three times;

A suspension of silk fibroin microspheres is formulated with deionized water, placed in a refrigerator at 4° C. or stored after vacuum freeze drying.

Figure 18:
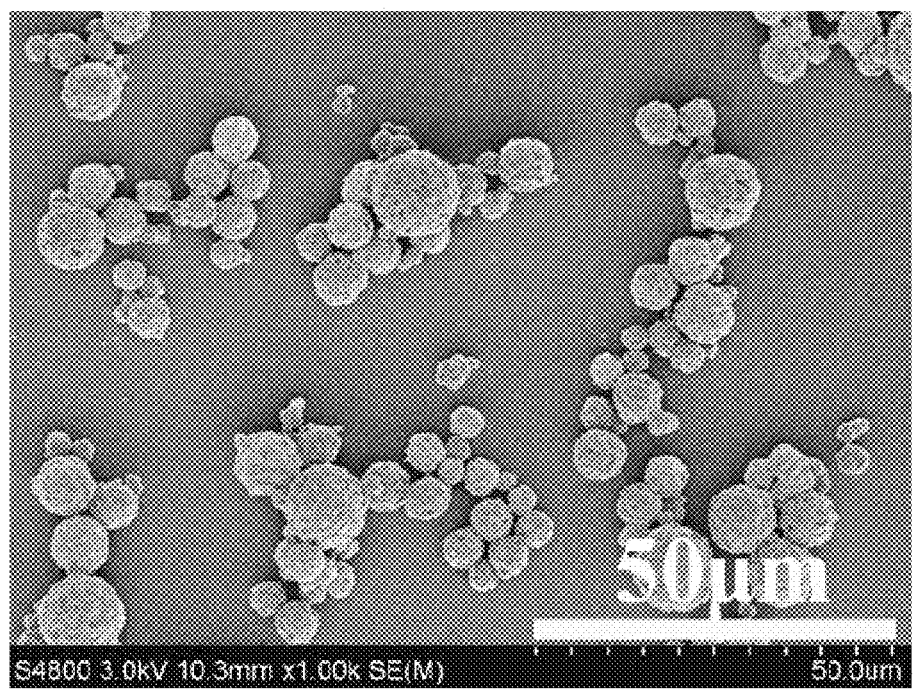
FIG. 18 is a scanning electron micrograph of silk fibroin microspheres prepared by blending a PEG solution of a molecular weight of 4000 and a concentration of 60% with a 5 wt % silk fibroin solution.

Refer to FIG. 18, which is a scanning electron micrograph of microspheres prepared in this example. It can be seen from the figure that, after the solution placed in the oven at 60° C. is removed and then mixed and incubated at room temperature, microspheres can be formed within 1 h.

2.5.3 Polyethylene glycol solutions of a molecular weight of 4000 and 6000 and a concentration of 30% are formulated;

The 30 wt % silk fibroin solution above is diluted to 5 wt %;

The two solutions above are placed in an oven at 60° C. for 30 min;

The two solutions above are taken and mixed in a 2/1 ratio (polyethylene glycol/silk fibroin) and incubated at room temperature for 24 h;

After incubation is completed, a centrifuge tube is placed in a centrifuge for centrifugation under conditions: room temperature, 10 min, 12000 rpm/min;

Washing is performed by adding deionized water, the supernatant is removed, and the centrifugation and washing operations are repeated three times;

A suspension of silk fibroin microspheres is formulated with deionized water, placed in a refrigerator at 4° C. or stored after vacuum freeze drying.

Figure 19:
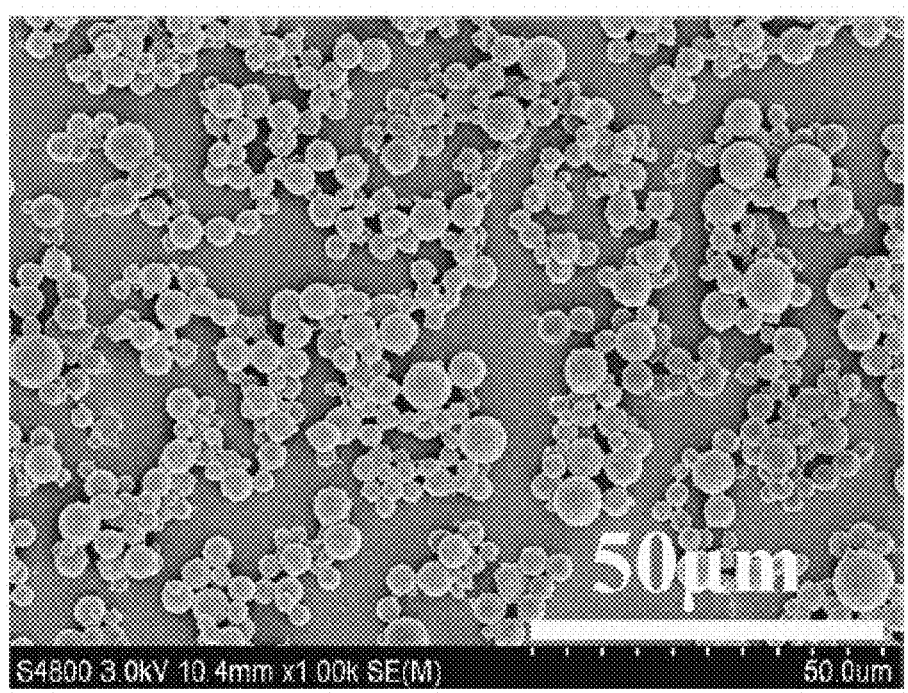
FIG. 19 is a scanning electron micrograph of silk fibroin microspheres prepared by blending a PEG solution of a molecular weight of 4000 and a concentration of 30% with a 5 wt % silk fibroin solution.
Figure 20:
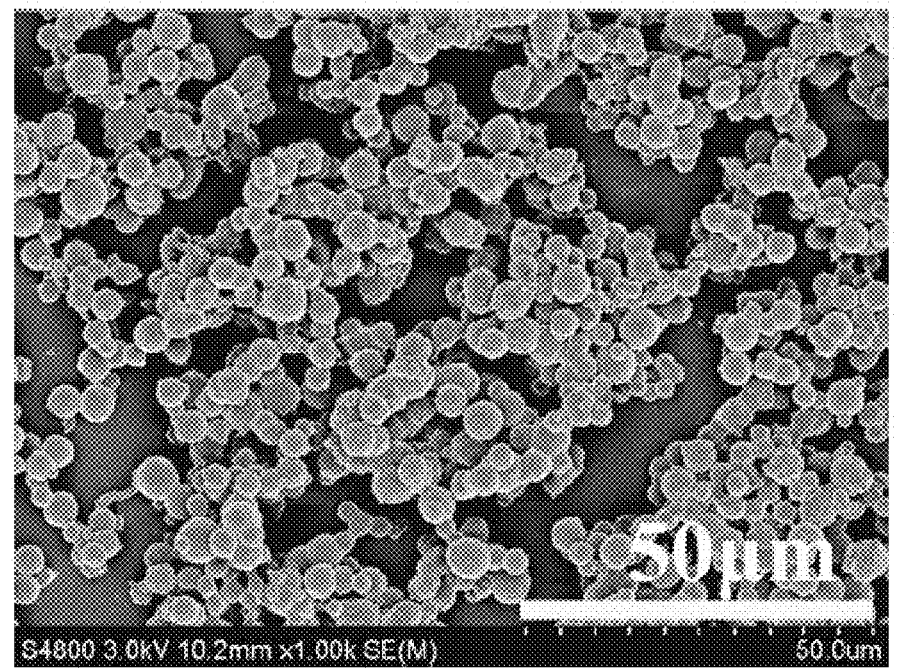
FIG. 20 is a scanning electron micrograph of silk fibroin microspheres prepared by blending a PEG solution of a molecular weight of 6000 and a concentration of 30% with a 5 wt % silk fibroin solution.

Refer to FIGS. 19 to 20, which are scanning electron micrographs of microspheres prepared in this example. It can be seen from the figures that, after the solution placed in the oven at 60° C. is removed and then incubated at room temperature, and microspheres can be formed within 24 h, with good dispersibility of fibroin microspheres.

2.6 Silk Fibroin Microspheres Loaded with Curcumin 0.5 mg and 0.9 mg of curcumin are weighed respectively;

1 mL of polyethylene glycol solutions of 50 wt % and molecular weight 10000 are formulated respectively to dissolve the curcumin above;

The 30 wt % silk fibroin solution above is diluted to 5 wt % and 9 wt % for 1 mL each;

The 5 wt % silk fibroin solution is added into the polyethylene glycol solution containing 0.5 mg/mL of curcumin in equal volumes, and the 9 wt % silk fibroin solution is added into the polyethylene glycol solution containing 0.9 mg/mL of curcumin in equal volumes; the blends are gently pipetted up and down to be mixed uniformly;

The curcumin-polyethylene glycol-silk fibroin blends are incubated at room temperature for 2 h;

After incubation is completed, a centrifuge tube is placed in a centrifuge for centrifugation under conditions: room temperature, 10 min, 12000 rpm/min;

Washing is performed by adding deionized water, the supernatant is removed, and the centrifugation and washing operations are repeated three times;

The curcumin-silk fibroin microspheres in suspension are stored after vacuum freeze drying;

1 mg of the curcumin-silk fibroin microspheres prepared with the 5 wt % and 9 wt % silk fibroin solutions are weighed respectively and added with 1 mL of a methanol solution (three samples weighed for each group);

A centrifuge tube is shaken on a shaker for 10 min, and then is rotated in a static mixer for 2 h;

The centrifuge tube is removed and centrifuged under conditions: room temperature, 10 min, 12000 rpm/min;

The supernatant is taken and determined for the absorbance of curcumin at 490 nm with a microplate reader. The content of curcumin in the silk fibroin microspheres is calculated by comparing with the absorbance-concentration standard curve of curcumin to calculate the drug loading rate;

It can be concluded that the drug loading rate of the curcumin-silk fibroin microspheres prepared with the 5 wt % silk fibroin solution is 0.27%±0.07%, and the drug loading rate of the curcumin-silk fibroin microspheres prepared with the 9 wt % silk fibroin solution is 0.51%±0.15%.

Figure 21:
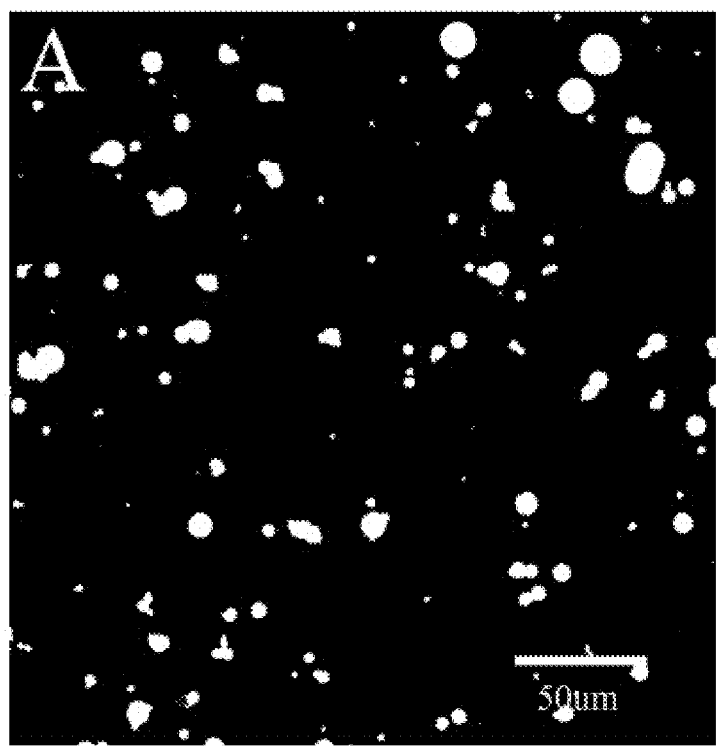
FIG. 21 shows the results of laser confocal microscopy (fluorescence) of curcumin-silk fibroin microspheres prepared using a 9 wt % silk fibroin solution.
Figure 22:
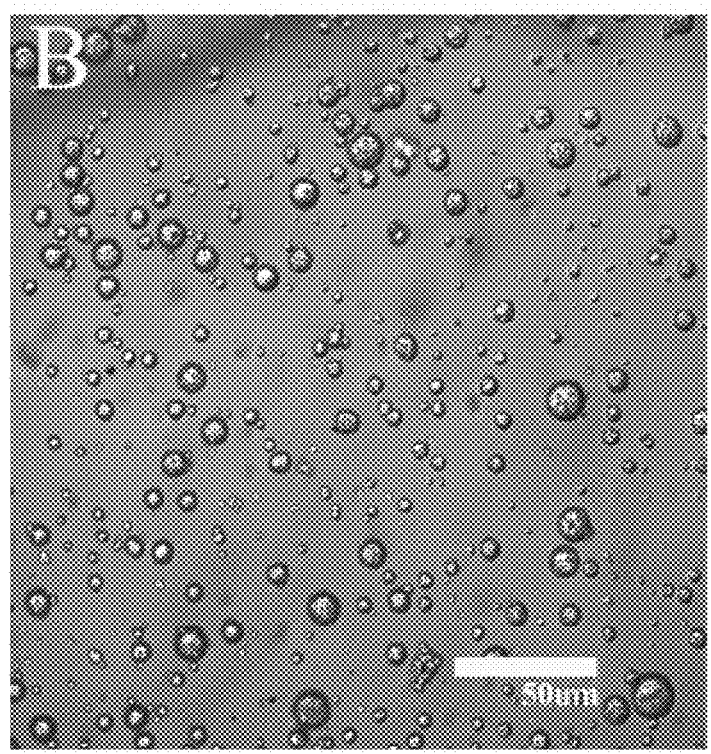
FIG. 22 shows the results of laser confocal microscopy (bright field) of curcumin-silk fibroin microspheres prepared using a 9 wt % silk fibroin solution.

Refer to FIGS. 21 to 22, which show the results of laser confocal microscopy of curcumin-silk fibroin microspheres prepared using the 9 wt % silk fibroin solution provided in this example.

In summary, the preparation of the freeze-dried powder of the present invention in a microsphere state has the following advantages:

1. The pharmaceutical adjuvant polyethylene glycol is selected to blend with a silk fibroin solution for preparing silk fibroin microspheres. The material is widely available and optimal use of resources can be made;

2. Both polyethylene glycol and silk fibroin have good biocompatibility, no organic solvent is added during the preparation, and the prepared silk fibroin microspheres have high bio-safety and can be directly used clinically;

3. Silk fibroin microspheres are rapidly prepared by direct mixing and incubation. No complex experimental devices are required, and drying into films and then dissolution are not required, so as to simplify the operation process and reduce the preparation time, such that industrialized production can be achieved;

4. Silk fibroin microspheres can be prepared at normal temperature, and do not need to be frozen in a refrigerator or dried in an oven, which not only saves energy, but also reduces production cost;

5. The particle size of the prepared silk fibroin microspheres is adjusted by the relative molecular weight and concentration of polyethylene glycol, the concentration of silk fibroin, and the temperature of both, thereby creating conditions for subsequent drug loading; and 6. The prepared silk fibroin microspheres can be used to encapsulate therapeutic drugs for sustained-release purpose. A hydrophobic (poorly water soluble) drug can be dissolved in a polyethylene glycol solution, and then mixed and incubated with a silk fibroin solution, and encapsulated in the silk fibroin microspheres through the weak intermolecular binding force of silk fibroin, thereby improving the drug loading rate of the hydrophobic drug.

Example 3

Figure 23:
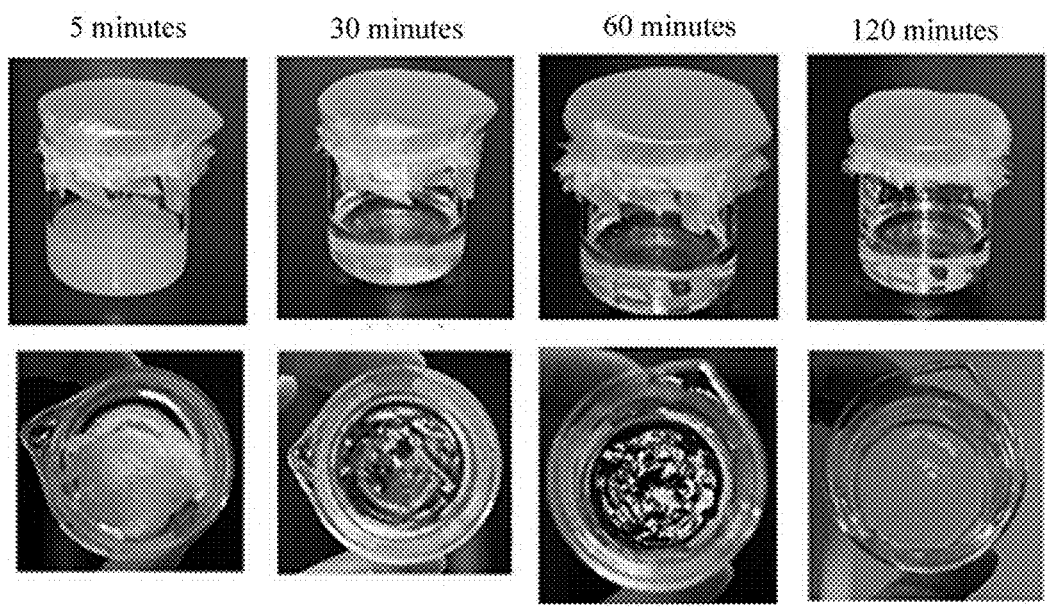
FIG. 23 shows the observation results of a silk fibroin solution at different dissolution times using a calcium chloride-containing ternary solution.

3.1 The present invention provides a preparation method of a silkworm silk fibroin solution, with silk dissolution using a calcium chloride-containing ternary solution, including the steps as follows:

1) 110 g anhydrous calcium chloride is weighed and dissolved in 140 g purified water. After it is sufficiently dissolved and restored to room temperature, 92 g absolute ethanol is added to prepare a calcium chloride-containing ternary solution as a solvent;

2) 30 g chopped silkworm cocoon filaments are weighed, boiled in a 0.02 M aqueous sodium carbonate for 25-35 min to remove silk sericin, repeatedly scrubbed with deionized water three times, and then dried in a fume hood after washing with water is completed, for future use;

3) The air-dried degummed silk is dissolved in the ternary solution in a bath ratio of 1:25 under a constant temperature of 75-85° C. for 0.5-2 h. As shown in FIG. 23, it can be seen that 2 g of the degummed silk can be completely dissolved with 20 ml the calcium chloride-containing ternary solution over 30 min;

4) The silk fibroin solution is transferred into a dialysis tube having a molecular weight cut-off of 8000-14000, subjected to gradient dialysis using urea, SDS or guanidine hydrochloride solutions in a concentration gradient from high to low, for 1-5 h per dialysis, and finally dialyzed against deionized water for 30 h, during which water is changed many times, giving a dialysate; and 5) The dialysate is transferred into a centrifuge tube, and centrifuged at 9000 rmp for 20 min (repeatedly 2 times) to remove insolubles, giving a silk fibroin solution having a concentration of 3-4% (w/v), which is stored in a refrigerator at 4° C.

In the steps above, the gradient dialysis may be performed using the concentration gradient below:

dialysis against 4 M urea, 2 M urea, 1 M urea, and water;
dialysis against 4 M urea, 2 M urea, and water;
dialysis against 4 M urea, 1 M urea, and water;
dialysis against 2 M urea or guanidine hydrochloride, 1 M urea or guanidine hydrochloride, and water;
dialysis against 2 M urea or guanidine hydrochloride, and water;
dialysis against 1 M urea or guanidine hydrochloride, and water;
dialysis against 2% SDS, 1% SDS, and water;
dialysis against 1% SDS, and water; and
dialysis against water.

3.2 The present invention provides a preparation method of a silkworm silk fibroin solution, in which degumming, silk dissolution, and renaturation processes are substantially the same as those in 3.1 and are not repeatedly described herein.

The difference is that in this example, silk dissolution is performed in a bath ratio of 1:10 at a temperature of 60° C. for 0.5 h, followed by 1 h per dialysis.

For the silk fibroin solution obtained by degumming, silk dissolution, and renaturation processes: the silk dissolution time is short, the silk dissolution temperature is low, the molecular weight of silk fibroin is large, and also, due to short dialysis time, the renaturation of silk fibroin has a general effect.

3.3 The present invention provides a preparation method of a silkworm silk fibroin solution, in which degumming, silk dissolution, and renaturation processes are substantially the same as those in 3.1 and are not repeatedly described herein.

The difference is that in this example, silk dissolution is performed in a bath ratio of 1:50 at a temperature of 85° C. for 24 h.

For the silk fibroin solution obtained by degumming, silk dissolution, and renaturation processes: the silk dissolution time is long, the silk dissolution temperature is high, the molecular weight of silk fibroin is small, and also, due to dialysis time of more than 5 h, it is difficult to further improve the renaturation effect of silk fibroin.

3.4 The present invention provides a preparation method of a silkworm silk fibroin solution, with gradient dialysis of a silk fibroin solution using urea in a concentration gradient from high to low, including the steps as follows:

(1) The silk fibroin solution is obtained in the same process as that in 3.1;

(2) The silk fibroin solution is transferred into a dialysis tube having a molecular weight cut-off of 8000-14000, subjected to gradient dialysis using urea solutions at the maximum concentration of 4 M, 2 M and 1 M respectively, for 3 h per dialysis, and finally dialyzed against deionized water for 30 h, during which water is changed many times, giving a dialysate;

specifically, the gradient dialysis is performed using the concentration gradient below:

dialysis against 4 M urea, 2 M urea, 1 M urea, and water;
dialysis against 2 M urea, 1 M urea, and water;
dialysis against 1 M urea, and water; and
dialysis against water; and (3) The dialysate is poured into a centrifuge tube, and centrifuged at 9000 rmp for 20 min (repeatedly 2 times) to remove insolubles, giving a silk fibroin solution having a concentration of 3-4% (w/v), which is stored in a refrigerator at 4° C.

Figure 24:
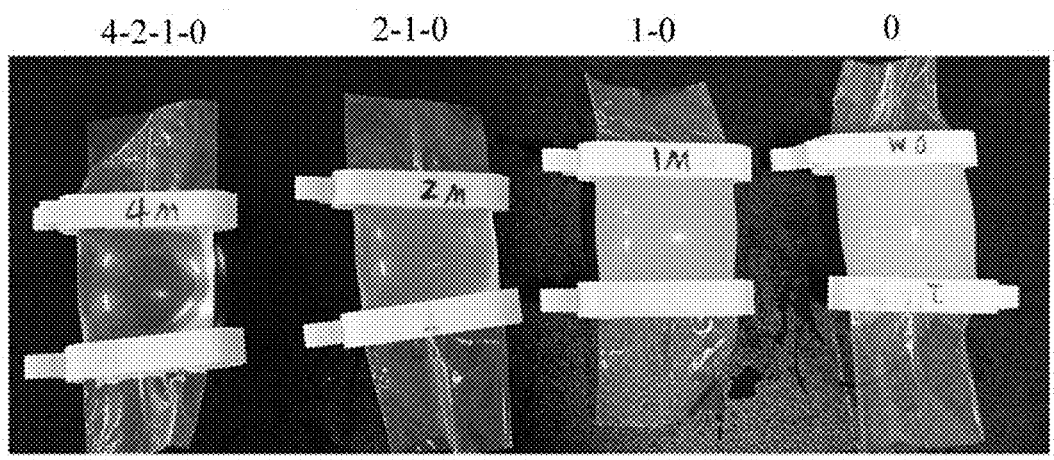
FIG. 24 is a comparison diagram showing the renaturation process of silk fibroin solutions.

As shown in FIG. 24, 4 schemes are employed: 1) dialysis against 4 M urea, 2 M urea, 1 M urea, and water, respectively; 2) dialysis against 2 M urea, 1 M urea, and water, respectively; 3) dialysis against 1 M urea, and water, respectively; and 4) dialysis against water directly. The 4 schemes correspond to 4-2-1-0, 2-1-0, 1-0, and 0 in the figure, respectively. It can be seen that, for different dialysis processes, the silk fibroin solutions appear different colors, from off-white to light yellow, indicating that the dispersion state of silk fibroin is different.

Figure 25:
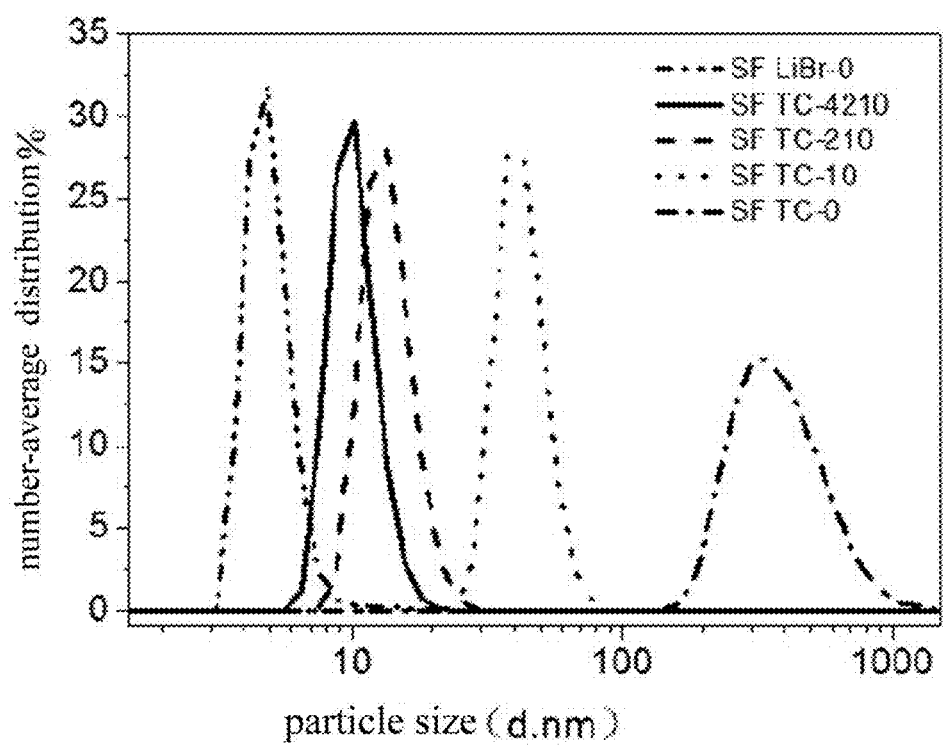
FIG. 25 shows the particle size of silk fibroin solutions determined by the dynamic light scattering technique.

As shown in FIG. 25, 5 schemes are employed: 1) dialysis against 4 M urea, 2 M urea, 1 M urea, and water, respectively; 2) dialysis against 2 M urea, 1 M urea, and water, respectively; 3) dialysis against 1 M urea, and water, respectively; 4) dialysis against water directly; and 5) the silk fibroin solution obtained with the 9.3 M aqueous lithium bromide solution. The 5 schemes correspond to 4-2-1-0, 2-1-0, 1-0, 0, and LiBr in the figure, respectively. It can be seen that when dialysis against water directly is used in the conventional preparation method of silk fibroin, a number of aggregates are present in the solution, while the samples with gradient dialysis have similar results to those with silk dissolution using LiBr and the silk fibroin molecules are present in a monodisperse form.

3.5 The present invention provides a preparation method of a silkworm silk fibroin solution, with gradient dialysis of a silk fibroin solution using SDS or guanidine hydrochloride solutions in a concentration gradient from high to low, including the steps as follows:

(1) The silk fibroin solution is obtained in the same process as that in 3.1;

(2) The silk fibroin solution is transferred into a dialysis tube having a molecular weight cut-off of 8000-14000, subjected to gradient dialysis using guanidine hydrochloride solutions at the maximum concentration of 2 M and 1 M or SDS solutions of 2% and 1%, respectively, for 3 h per dialysis, and finally dialyzed against deionized water for 30 h, during which water is changed many times, giving a dialysate;

specifically, the gradient dialysis is performed using the concentration gradient below:

dialysis against 2 M guanidine hydrochloride, 1 M guanidine hydrochloride, and water;
dialysis against 2 M guanidine hydrochloride, and water;
dialysis against 1 M guanidine hydrochloride, and water;
dialysis against 2% SDS, 1% SDS, and water;
dialysis against 1% SDS, and water; and
dialysis against water; and (3) The dialysate is poured into a centrifuge tube, and centrifuged at 9000 rmp for 20 min (repeatedly 2 times) to remove insolubles, giving a silk fibroin solution having a concentration of 3-4% (w/v), which is stored in a refrigerator at 4° C.

The results of renaturation of the silk fibroin solution with SDS or guanidine hydrochloride solutions are consistent with those with urea in the example 2. Most preferably, the gradient dialysis is dialysis against 2 M guanidine hydrochloride, 1 M guanidine hydrochloride, and water; and dialysis against 2% SDS, 1% SDS, and water.

Figure 26:
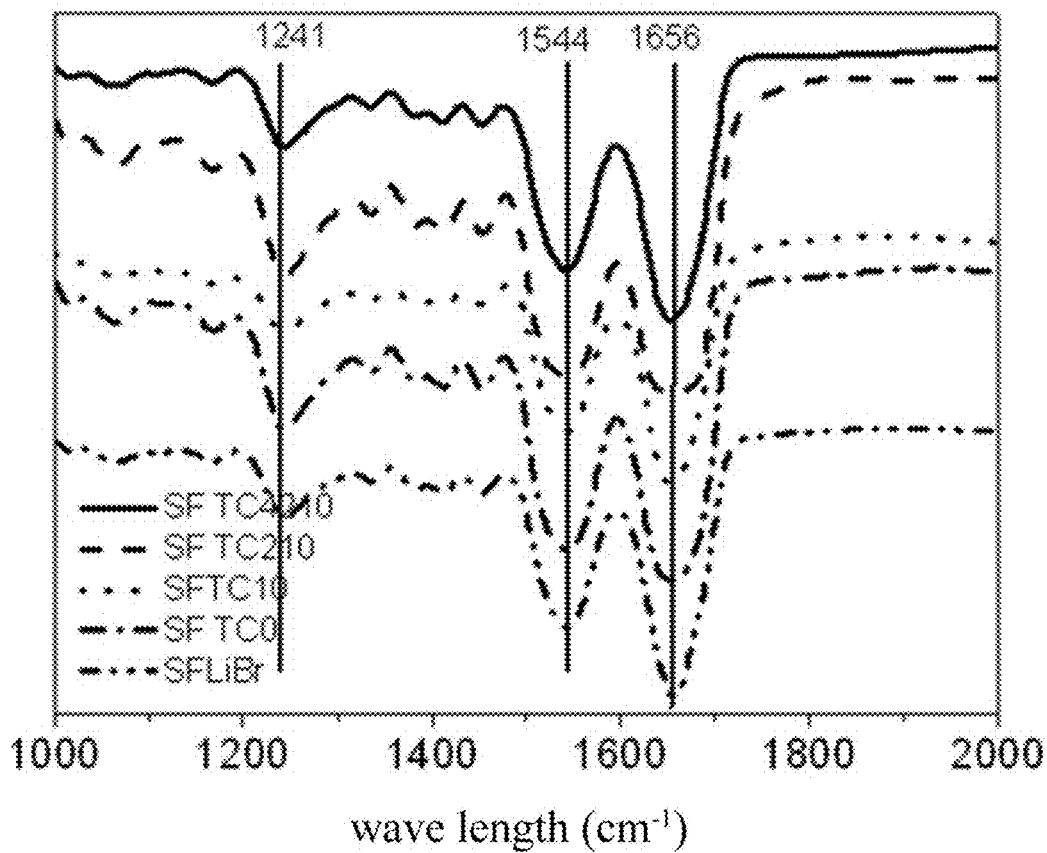
FIG. 26 shows the Fourier-Transform Infra-Red spectrum of regenerated silk fibroin solutions.

3.6 Silk fibroin is essentially consisted of 18 amino acids such as glycine, alanine, serine, and its characteristic amino acids bear amino group and carboxyl group and are amphiphilic in nature. The silk fibroin solution is detected by the Fourier-Transform Infra-Red spectroscopy, and it is found that the absorption peak at 1660 cm$^{-1}$ is the random coil structure, the absorption peaks at 1655 cm$^{-1}$ and 1546 cm$^{-1}$ are mainly the α-helix structure, and the absorption peaks at 1630 cm$^{-1}$ and 1520 cm$^{-1}$ are the β-sheet structure. As shown in FIG. 26, 5 schemes are employed: 1) dialysis against 4 M urea, 2 M urea, 1 M urea, and water, respectively; 2) dialysis against 2 M urea, 1 M urea, and water, respectively; 3) dialysis against 1 M urea, and water, respectively; 4) dialysis against water directly; and 5) the silk fibroin solution obtained with the 9.3 M aqueous lithium bromide solution. The 5 schemes correspond to 4-2-1-0, 2-1-0, 1-0, 0, and LiBr in the figure, respectively. The silk fibroin solution obtained in the example 2 is detected by the Fourier-Transform Infra-Red spectroscopy, and it is found that the regenerated silk fibroin has significant absorption peaks at 1544 cm$^{-1}$ and 1656 cm$^{-1}$. As a result, silk fibroin prepared in this study is mainly the α-helix structure.

Figure 27:
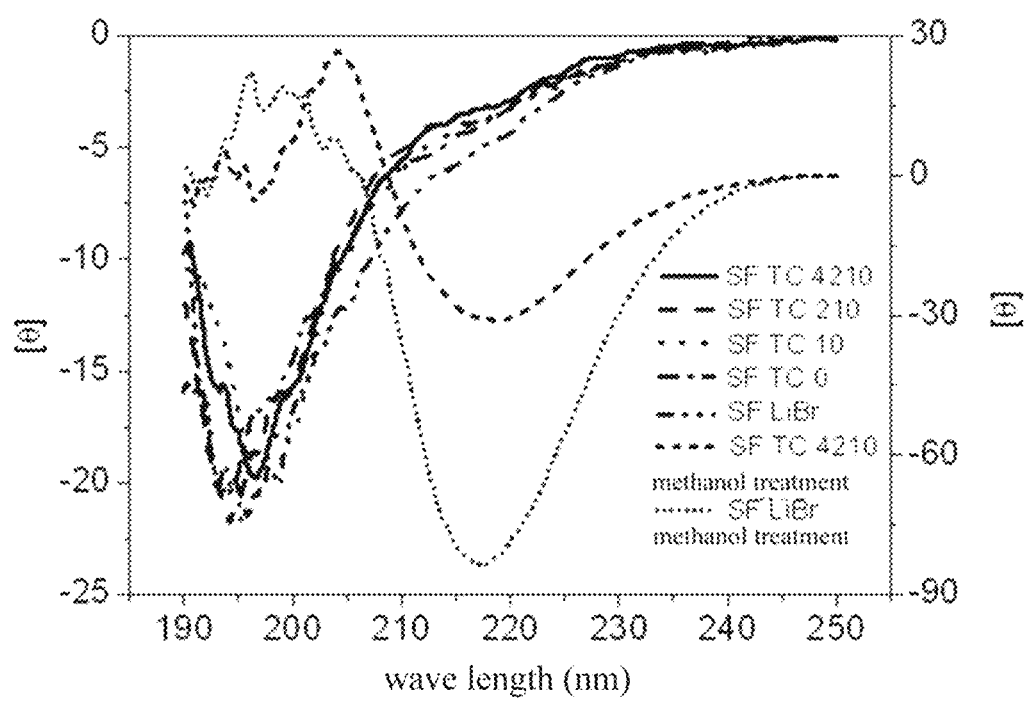
FIG. 27 shows the circular dichroism spectrum of regenerated silk fibroin solutions.

The circular dichroism spectrum in FIG. 27 verifies the conclusions above. 7 schemes are employed: 1) dialysis against 4 M urea, 2 M urea, 1 M urea, and water, respectively; 2) dialysis against 2 M urea, 1 M urea, and water, respectively; 3) dialysis against 1 M urea, and water, respectively; 4) dialysis against water directly; 5) the silk fibroin solution obtained with the 9.3 M aqueous lithium bromide solution; 6) denaturation with methanol of the silk fibroin solution after dialysis against 4 M urea, 2 M urea, 1 M urea, and water; and 7) denaturation with methanol of the silk fibroin solution obtained with the 9.3 M aqueous lithium bromide solution. The 5 schemes correspond to 4-2-1-0, 2-1-0, 1-0, 0, LiBr, 4-2-1-0-methanol, and LiBr-methanol in the figure, respectively. For silk fibroin, the α-helix and random coil structure has a strong circular dichroism signal at about 295 nm, and the β-sheet structure has a strong signal at about 220 nm. It can be seen from the figure that, silk fibroin prepared with different urea concentration gradients is the α-helix and random coil structure, and after denaturation with methanol, is the β-sheet structure, having a strong signal at 220 nm. In connection with the color of the silk fibroin solutions in FIG. 24, when dialysis against water directly is used for the silk fibroin solution obtained by dissolving degummed silk with the ternary solution, a number of aggregates occur, while the silk fibroin solution is clear without aggregates after gradient dialysis.

3.7 The present invention provides an identification method of a silkworm silk fibroin solution, including the following steps:

(1) weighing and dissolving 484 g urea in 1 L deionized water to formulate an 8 M urea solution;

(2) adding the silk fibroin solution into the 8 M urea solution, incubating in a bath ratio of 1:10 in a water bath at 37° C. for 30 min, and centrifuging at 10000 rpm for 20 min to collect the supernatant;

(3) Elution conditions:
Apparatus: protein chromatography and purification apparatus;
Column: Superdex 200 10/300 GL;
Column equilibration: 5× column volume of 4 M urea, flow rate 0.5 ml/min;
Sample loop: 10-100 μl sample loop;
Eluant: 4 M urea solution;
Flow rate: 0.5 ml/min;
Detection parameter of detector: UV-A280.

(4) Marker proteins: conalbumin: 75 kDa; ferritin: 440 kDa; and thyroglobulin: 669 kDa.

Figure 28:
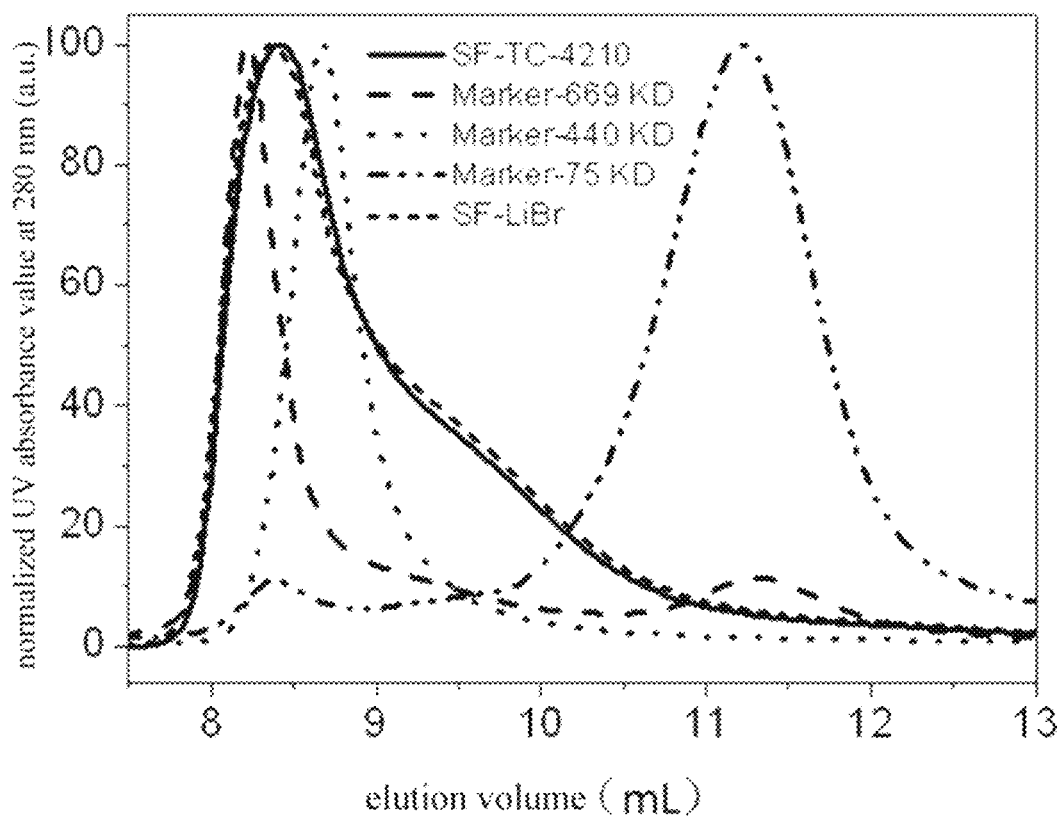
FIG. 28 shows the chromatography elution profile of regenerated silk fibroin solutions.
Figure 29:
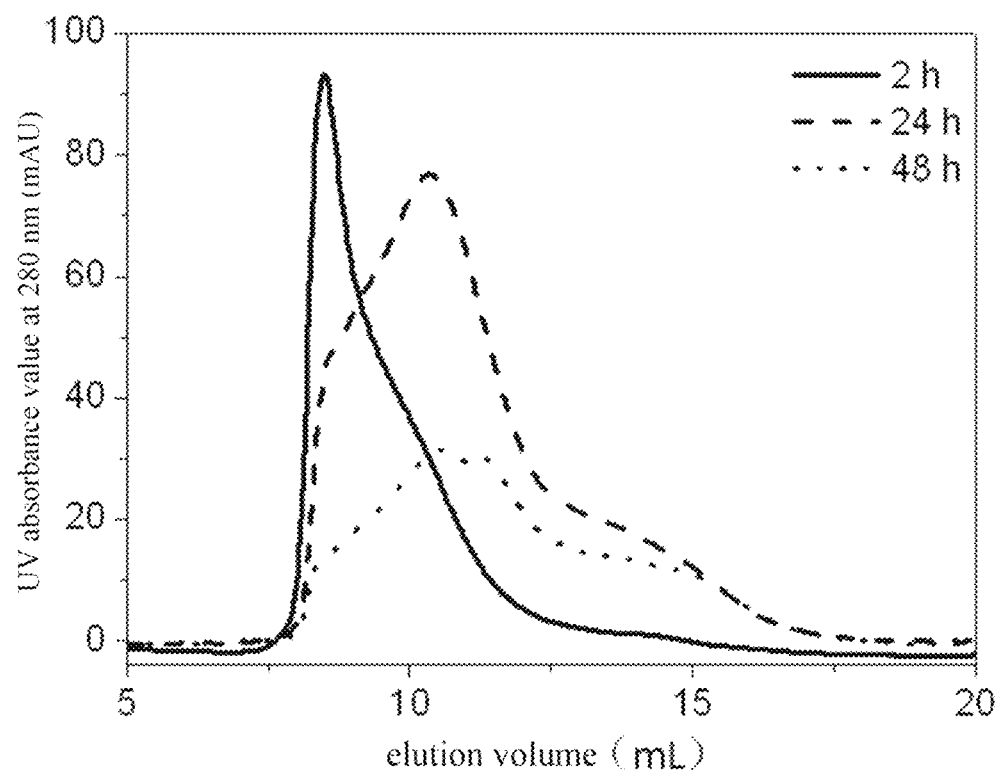
FIG. 29 is a comparison diagram showing the molecular weight distribution of a silk fibroin solution at different dissolution times using a calcium chloride-containing ternary solution.

Referring to FIG. 28, the elution profiles using the protein chromatography system after the silk fibroin solution obtained with the methods in the example 2 of the present invention, and the marker proteins conalbumin, ferritin and thyroglobulin are treated with the 8 M urea solution are shown. It can be seen from the figure that, greater the molecular weight, shorter the elution time. The elution time of silk fibroin is between that of ferritin of molecular weight 440 kDa and that of thyroglobulin of molecular weight 669 kDa. It can be concluded from the separation principle of molecular sieve chromatography column that, the molecular weight of silk fibroin prepared by the present invention is between 440 kDa and 669 kDa, which is larger than the theoretical value 405 kDa of the molecular weight of silk fibroin. This is because after silk fibroin is treated with urea, the intramolecular hydrogen bond is broken, the molecules are linear and the volume is larger than that of the globular protein of the same molecular weight. Therefore, it can be concluded from this study that the molecule of silk fibroin prepared by the present invention is a near-native macromolecular polymer. FIG. 29 shows the elution profiles using the protein chromatography system of silk fibroin solutions obtained at different dissolution times by dissolving degummed silk with a ternary solution. It can be seen from the figure that with increase in silk dissolution time, the elution time gradually increases, the elution peak gradually becomes wider, the elution peak of high molecular weight substance disappears, and the elution peak of low molecular weight substance gradually becomes apparent. That is, the molecular weight of silk fibroin gradually decreases. Therefore, according to different silk dissolution times, silk fibroin of different molecular weights can be prepared by the present invention.

Example 4

The controlled-release or sustained-release silk fibroin gel formulation for treating an inner ear disease of the present invention includes a formulation body, including a gel-state carrier, and a drug dispersed in or adsorbed to the carrier. The drug is a drug for treating an inner ear disease, and the carrier is a silk fibroin gel. The silk fibroin gel is prepared from a silk fibroin solution by induction gelling. The induction gelling includes pH change, ultrasonic vibration, electrophoresis, blending with horseradish peroxidase (HRP)-hydrogen peroxide ($H_2O_2$), and blending with low-molecular weight polyethylene glycol (PEG).

The drug is classified into a water soluble drug and a poorly water soluble drug. Thus, the formulation body is prepared from the drug in an aqueous solution or insoluble particles by mixing with the silk fibroin solution and then by the induction gelling. Considering extended release required for the drug, a preferred drug form is a poorly water soluble drug and a more preferred one is a poorly water soluble drug in a spherical shape (micronized drug). The poorly water soluble drug may be prepared into microspheres by spray drying and the like. Considering the effect of extended release, the drug formulation may be further pretreated, namely, the surface of microspheres of the therapeutic drug is coated with silk fibroin, which can more effectively promote the sustained-release effect of the drug in the process of gel degradation. The poorly water soluble drug is suspended in a suitable solvent as microspheres, and then mixed with the silk fibroin solution followed by induction gelling. The suitable solvent includes, but is not limited to: water, organic solvents, solubilizers, tackifiers, and penetration enhancing agents.

According to different dosages of different drugs, in a drug solution, the drug concentration ranges from 0.5%-15% (w/v), in which the concentration for low loading is 0.5-2%; the concentration for medium loading is 2-5%; and the concentration for high loading is 5-15%. The concentration of silk fibroin in the formulation body is 1-30%; preferably, the concentration of silk fibroin in the formulation body is 7.5-15%.

Inner ear diseases for which the controlled-release or sustained-release silk fibroin gel formulation for treating an inner ear disease of the present invention may be used, include Meniere's Disease, sudden sensorineural hearing loss (SSNHL), Meniere's syndrome, sensorineural hearing loss, and autoimmune inner ear disease (AEID); and accordingly, the used drug includes one or more of dexamethasone, betamethasone, prednisolone, methylprednisolone, desoxycorticosterone, 11-desoxycorticosterone, 18-H-11-desoxycorticosterone, beclomethasone, triamcinolone acetonide, and chemical synthetic derivatives thereof.

For the controlled-release or sustained-release silk fibroin gel formulation for treating an inner ear disease of the present invention, the drug action site is inner ear, the pharmaceutical preparation is a gel state and applied on and around the round window membrane of the cochlea, and the pharmaceutical preparation may be injected through the round window niche of the cochlea and/or injected through the tympanum. It is used in two ways: in situ gelling and pre-gelling; both are different in that for the pre-gelling, gelling is performed in vitro followed by injection or implantation into the inner ear, and for the in situ gelling, a drug is injected in suspension into the entire space of the round window niche and then a semi-solid gel of a suitable form is formed, thereby maximizing contact with the surface of the round window membrane. When the drug formulation is in situ gelling, in solution, the administration mode includes, but is not limited to, administration by injecting into the tympanum using a common syringe and a microneedle, and administration using a micro-syringe.

For the controlled-release or sustained-release silk fibroin gel formulation for treating an inner ear disease of the present invention, if blending with low-molecular weight polyethylene glycol (PEG) is employed and in situ gelling is used, the mechanism of action of the drug is that: after injection, the entire space of the round window niche is filled with the silk fibroin-polyethylene glycol (PEG) mixture, which in turn forms a semi-solid gel of a suitable form, thereby maximizing contact with the surface of the round window membrane; and with long-term attachment of the gel onto the round window membrane, the drug is continuously released and enters the inner ear to achieve the therapeutic effect on the disease. With the release of the drug, the gel is subjected to proteolytic degradation in vivo, and the degradation products are polypeptides and amino acids. The degradation time may be appreciated through experiments. The degradation starts at day 10, and only a small amount of the residual gel is present on the administration site at day 21, and also it is found that the controlled-release or sustained-release time of the drug can last for more than 10 days.

4.1 The present invention provides a method of preparing a controlled-release or sustained-release silk fibroin gel formulation for treating an inner ear disease, including the following steps:

1) mixing: the drug for treating an inner ear disease in an aqueous solution or insoluble microspheres is uniformly mixed with the silk fibroin solution to give a drug suspension; and 2) gelling: the drug suspension is prepared into the formulation body by induction gelling.

The induction gelling includes pH change, ultrasonic vibration, electrophoresis, blending with horseradish peroxidase (HRP)-hydrogen peroxide ($H_2O_2$), and blending with low-molecular weight polyethylene glycol (PEG).

The operation procedures of different induction gelling modes are shown below, and the comparison results are shown in table 1:

(a) Preparation of a Silk Fibroin Gel with pH Change 10 mL of a 5% (w/v) silk fibroin solution is added into a 20 mL small beaker, adjusted with a NaH2PO4-Na2HPO4 buffer to a pH of 5.2, and placed at room temperature overnight for slow gelling.

(b) Preparation of a Silk Fibroin Gel with Ultrasonic Vibration 5 mL of a 5% (w/v) silk fibroin solution is added into a 10 mL test tube, subjected to ultrasonic vibration with a JYD-900 intelligent ultrasonic cell disruptor at 500 w power for 30-60 sec, and then placed at room temperature (25° C.) for gelling.

(c) Preparation of a Silk Fibroin Gel with Electrophoresis

Electrodes are dipped into an 8% (w/v) aqueous silk fibroin solution, and powered on under 25 V DC for 3 min. Due to a high water content of the silk fibroin solution, hydrolysis can occur during the power on process, generating oxygen and hydrogen, and thus, as the power on proceeds, bubbles appear at both electrodes. Also, the gelling phenomenon occurs at the anode position.

(d) Gelling with Horseradish Peroxidase (HRP)-Hydrogen Peroxide ($H_2O_2$)

HRP freeze-dried powder is added into deionized water to form a 1000 U/ml solution, and then a suitable amount of the HRP solution is added into a 3% (w/v) silk fibroin solution to a final concentration of HRP in the solution of 10 U/ml. Then, a $H_2O_2$ solution is added into the silk fibroin solution at 10 µl/ml to reach a final concentration of $H_2O_2$ of 165 nM to prepare a gel after mixing.

(e) Gelling with Low-Molecular Weight Polyethylene Glycol (PEG)

A 15% (w/v) silk fibroin solution is mixed with an 80% (w/w) PEG 400 solution in equal volumes, and incubated at 37° C. for gelling.

TABLE 3

Comparison of different preparation methods of a silk fibroin gel

| Name | Preparation method | Determination of the main crystalline structure by x-ray diffraction |
|---|---|---|
| pH change | a NaH$_2$PO$_4$—Na$_2$HPO$_4$ buffer is added into a silk fibroin solution to adjust the pH of the solution to 5.2, and the solution is gelled | Silk II |
| Ultrasonic vibration | a silk fibroin solution is sonicated at 800 w power for gelling | Silk II |
| electrophoresis | an aqueous silk fibroin solution is electrolyzed under 25 V DC voltage, and the gelling phenomenon firstly occurs at the anode position. | Silk II |
| Gelling with HRP- | an HRP powder is added into a silk fibroin solution, added with a H$_2$O$_2$ | Silk II |

TABLE 3-continued

Comparison of different preparation methods of a silk fibroin gel

| Name | Preparation method | Determination of the main crystalline structure by x-ray diffraction |
|---|---|---|
| H₂O₂ Gelling with LMW-PEG | solution, and then the solution is gelled. a silk fibroin solution is mixed with a low-molecular weight PEG solution, and gelled at 37° C. | Silk II |

The main structure after gelling with various methods is detected by x-ray diffraction, and it is found that the main structures all are Silk II. The content of the Silk II crystal structure is the most important factor of determining the mechanical strength and degradation rate of silk fibroin biomaterials and the sustained-release or controlled-release properties of drugs, and thus, it can be known that there is no difference in material properties between the silk fibroin gels prepared with different methods above. Because the gelling method with low-molecular weight PEG is more convenient, controllable, and safe and non-toxic in clinical application, in the following examples, the silk fibroin-PEG gelling method is used in induction gelling, and other methods will not be described. In addition, it is noted that when blending with low-molecular weight PEG is used in preparing a gel, the drug may be mixed with PEG, or mixed with silk fibroin and PEG simultaneously.

4.2 The present invention provides a method of preparing a controlled-release silk fibroin gel for treating an inner ear disease, which is applicable to preparation of different pharmaceutical formulations:

(a) Preparation of Silk Fibroin-PEG-mDEX (Micronized Dexamethasone)

an amount of mDEX microspheres are suspended in 0.5 ml of a 15% (w/v) aqueous silk fibroin solution, and then the suspension is mixed with 0.5 ml of an 80% (w/w) PEG400 solution in equal volumes for gelling.

(b) Preparation of Silk Fibroin-PEG-DA (Dexamethasone Acetate) Gel

A sterile DA solution is uniformly mixed with a high concentration of an aqueous silk fibroin solution to reach a certain drug loading and a final concentration of silk fibroin of 15% (w/v), and then mixed with an equal volume of an 80% (w/w) PEG400 solution for gelling.

(c) Preparation of Silk Fibroin-PEG-MPS (Dexamethasone Sodium Phosphate) Gel

A sterile DSP solution is uniformly mixed with a high concentration of an aqueous silk fibroin solution to reach a certain drug loading and a final concentration of silk fibroin of 15% (w/v), and then mixed with an equal volume of an 80% (w/w) PEG400 solution for gelling.

Due to different effects and dosages of different drugs, it is difficult to exemplify these one by one in the present invention, and thus, in subsequent examples, a detailed description is only provided taking preparation of silk fibroin-PEG-mDEX as an example.

4.3 The present invention provides a method of preparing a controlled-release or sustained-release silk fibroin gel formulation for treating an inner ear disease, for preparation of silk fibroin-PEG-mDEX:

(a) preparation of mDEX-silk fibroin coating: about 20 mg of mDEX is suspended in 1 ml of a 0.1% (w/v) silk fibroin solution. The suspension is shaken slowly at room temperature for 2 min. Then, the suspension of microspheres is sonicated for about 1 min to disperse the agglomerated microspheres. After further shaking for 2 min, the solution is centrifuged for 2 min (14000 rpm) to remove the upper silk fibroin solution. The microspheres are washed with water (1 ml×2), shaken for 1 min, and centrifuged. The washed microspheres are dried with nitrogen. The coating step above may be repeated many times, until a desired coating thickness and a corresponding drug release rate are obtained.

(b) preparation of silk fibroin-PEG-mDEX gel: the prepared mDEX coated with silk fibroin is suspended in 0.5 ml of a high concentration of an aqueous silk fibroin solution to a final concentration of silk fibroin of 15% (w/v), and then the suspension is mixed with 0.5 ml of an 80% (w/w) PEG400 solution in equal volumes for gelling.

It is noted that: the step b) may be used alone to prepare a silk fibroin-PEG-mDEX gel without silk fibroin coating, and may also be used in combination with the step a) to prepare a silk fibroin-PEG-mDEX gel with silk fibroin coating.

4.4 The present invention provides a method of preparing a controlled-release or sustained-release silk fibroin gel formulation for treating an inner ear disease, for preparation of silk fibroin-PEG-mDEX. The method is consistent with that in 4.3, except that:

the concentration of silk fibroin is adjusted to 1-30%; however, when the final concentration of silk fibroin is 1%, due to low gel concentration, the drug loading is poor and the drug release rate is fast, and when the final concentration of silk fibroin is 30%, due to high gel concentration, the drug loading is high, the adsorption of the drug is more pronounced, and the drug release rate is slow, and thus, it is preferred that the concentration of silk fibroin in the formulation body is 7.5-15%.

4.5 The present invention provides a controlled-release or sustained-release silk fibroin gel formulation for treating an inner ear disease, prepared with the preparation method in 4.3, and then being subjected to morphological examination of a silk fibroin-PEG-mDEX gel by SEM. The test method is as follows:

mDEX (0%, 1.5% loading) encapsulated with a silk fibroin-PEG gel (7.5% w/v) is prepared following the method in the example 4. 200 μl of the prepared solution is dropped into a 24-well plate, and placed in a 37° C. environment for incubation until the solution is gelled. The well plate is dipped into a glass beaker containing 1000 ml purified water, slowly stirred for above 24 h, during which water is changed 4 times, and the washed gel is frozen at −80° C. overnight and freeze-dried for 48 h. The sample is observed by SEM.

Figure 30:
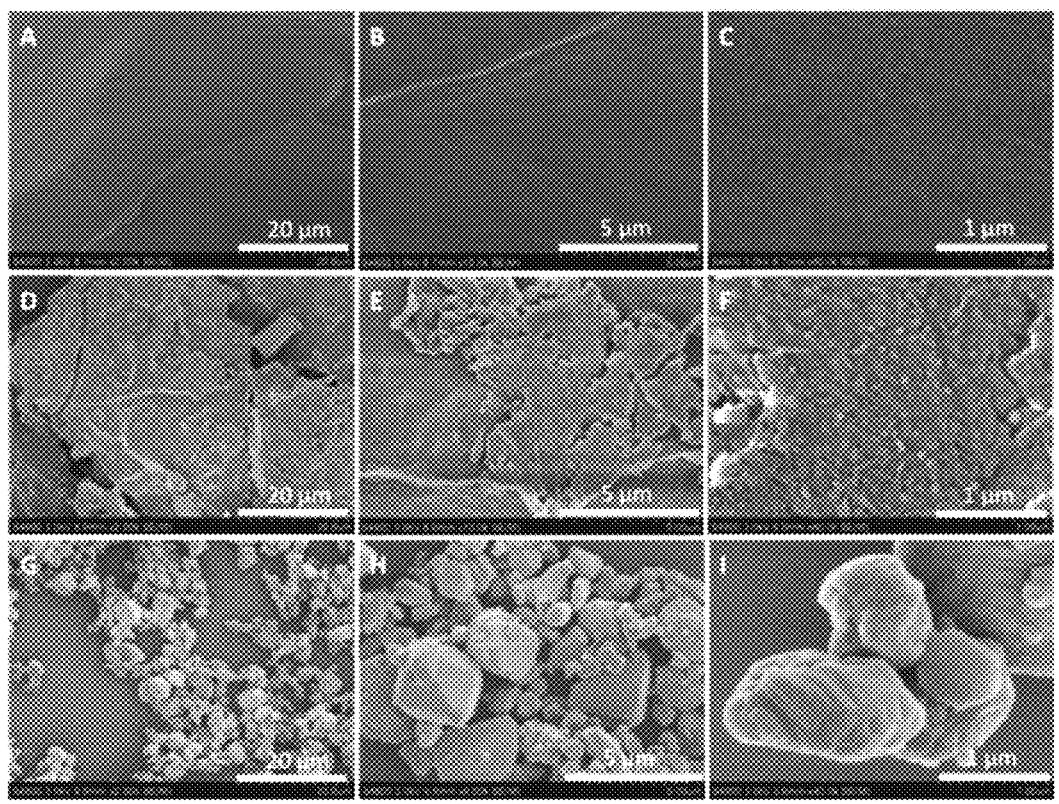
FIG. 30 shows the results of scanning electron microscopy of silk fibroin-PEG-mDEX gels.

As shown in FIG. 30, it is found from the morphological observation by SEM that PEG has been removed from the gel after washing with water, so that the remaining gel is a porous sponge-like structure. FIGS. 30A-30C show the results of scanning electron microscopy of silk fibroin-PEG gels without encapsulated mDEX at magnification factors of 20, 5 and 1 μm respectively. The silk fibroin-PEG gels without encapsulated mDEX have a porous structure, and have about 100 μm interconnected pores therein. FIGS. 30D-30F show the results of scanning electron microscopy of silk fibroin-PEG gels with encapsulated mDEX at magnification factors of 20, 5 and 1 μm respectively. The silk fibroin-PEG gels with encapsulated mDEX appear a similar porous stacked structure, and particulate mDEX (1-5 μm) is embedded within the silk fibroin matrix. FIGS. 30G-30I show the results of scanning electron microscopy of non-encapsulated water-insoluble mDEX microspheres at magnification factors of 20, 5 and 1 μm respectively. The mDEX particulates determined alone have the same size as that of particulates embedded within the silk fibroin gel, indicating that the gelling process of silk fibroin has no effect on the size and dispersibility of mDEX particulates.

4.6 The present invention provides the test results in controlled-release or sustained-release effect in vitro of the controlled-release or sustained-release silk fibroin gel formulation for treating an inner ear disease described in 4.3. The preparation method of a silk fibroin-PEG-mDEX gel is consistent with that provided in the example 4, except that the drug loading is changed, and the mDEX drug microspheres are not coated with silk fibroin. The in vitro release test is as follows:

The silk fibroin-PEG-mDEX gel is divided into low dosing (0.5%) and high dosing (2.5%) according to the drug loading of mDEX, and divided into in situ gelling group and pre-gelling group according to the gelling manner. For the in situ gelling group, 5 μl of a silk fibroin-PEG-mDEX solution is injected into a 2-ml micro-centrifuge tube through a 25 G needle, incubated at 37° C., and gelled within 30 min. For the pre-gelling group, a silk fibroin-PEG-mDEX solution contained in a syringe is incubated in a 37° C. environment and gelled within 30 min, and then 5 ml of the gel is injected into a 2-ml micro-centrifuge tube (without a needle). At the beginning of the experiment, each tube is added with 1 ml PBS (pH=7.4) buffer, and all the centrifuge tubes are shaken at 37° C. At 1, 6, and 24 h, and day 2, 3, 4, 5, 6, and 7, 0.95 ml of the release medium is withdrawn to a blank tube, and stored at 4° C. for LC/MS/MS detection. 0.95 ml of PBS (pH7.4) buffer is further supplemented in the original centrifuge tubes at a constant temperature.

Figure 31:
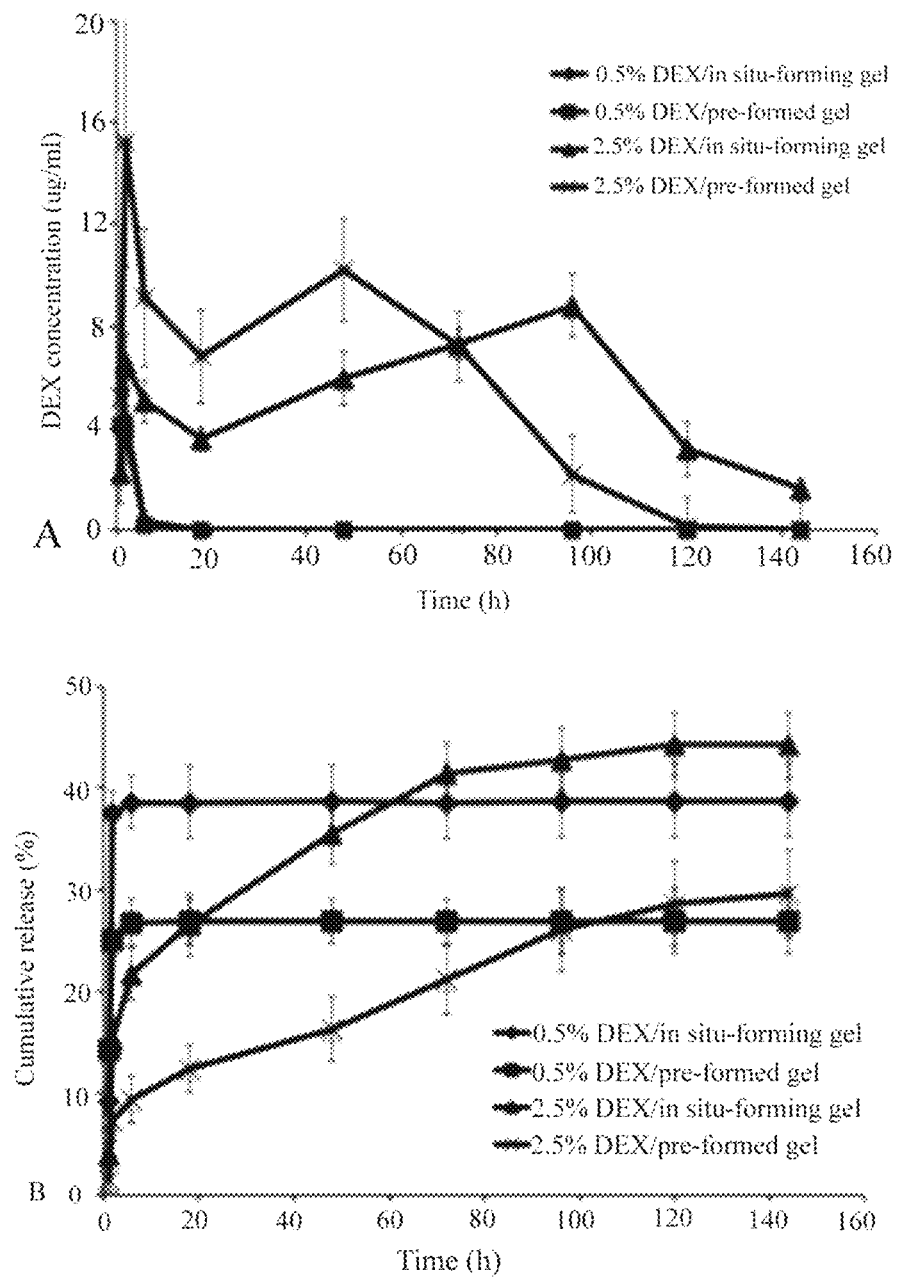
FIG. 31 shows the results of in vitro release test of silk fibroin-PEG-mDEX gels.

The results are shown in FIG. 31, in which FIG. 31A shows the comparison of detection results of DEX concentration (μg/ml) of 4 silk fibroin-PEG-mDEX gels in the release medium (PBS, pH7.4), at different times; and FIG. 31B shows the comparison of DEX accumulated release amounts of 4 silk fibroin-PEG-mDEX gels within 144 h, at different times. As shown in FIG. 31A, the silk fibroin-PEG-mDEX gel with a drug loading of 0.5% exhibits a fast release process at an initial stage, and for both the in situ gelling and pre-gelling modes, the drug concentration rapidly reaches the maximum concentration value (about 4 μg/ml) at 2 h and rapidly decreases to the baseline value after 6 h. When the drug loading of the gel is 2.5%, the duration of continuous release of DEX at a high concentration level is longer, in which for the in situ gelling mode, the DEX concentration varies from 5-10 μg/ml within 96 h and decreases to 1.6 μg/ml at 144 h; for the pre-gelling mode, the DEX concentration varies from 5-10 μg/ml within 72 h and decreases to 2.2 μg/ml at 96 h. When the mDEX drug loading is 0.5%, the accumulated release amounts for the in situ gelling and pre-gelling modes at 2 h are 38% and 25%, respectively (FIG. 31B). When the mDEX drug loading is 2.5%, both the in situ gelling and pre-gelling modes reach nearly zero order release, and after 144 h, the release rates are close to 44% and 30%, respectively (FIG. 31B).

4.7 The present invention provides the test results in controlled-release or sustained-release effect in vivo of the controlled-release or sustained-release silk fibroin gel formulation for treating an inner ear disease described in 4.3. The preparation method of a silk fibroin-PEG-mDEX gel is consistent with that provided in the example 4, except that the drug loading and the silk fibroin concentration are changed. The in vivo pharmacokinetic test is as follows:

(a) Otologic Surgery:
Method:
Silk fibroin-PEG-mDEX gels have a silk fibroin concentration of 7.5% (w/v) and an mDEX loading of 0.5% and 2.5% (w/v), for in vivo test. For a control group, 0.5% and 2.5% mDEX solutions are prepared by suspending mDEX in 10 mM PBS (pH7.4). The overall process is operated on a sterile console. Guinea pigs are anesthetized by intraperitoneal injection of 1% pentobarbital sodium (35 mg/kg). The animals need to be placed on a heating pad (38° C.) to maintain the body temperature throughout the operation, are locally anesthetized by subcutaneous injection of 1% lidocaine. The otic vesicle is exposed by a retroauricular surgery and a small hole of 3 mm in diameter is made on the otic vesicle to clearly see the round window niche. 10 μl of an mDEX suspension (control group) or a silk fibroin-PEG-mDEX suspension is dropped on the round window membrane with a tuberculin syringe (27 G needle), and after injection, the guinea pigs are fixed at the current position for about 30 min to await gelling of the solution, and the holes are closed with sutures and sealed with a dental cement.

(b) Sampling and Detection of DEX Concentration
Method: guinea pigs are divided into 2 groups (n=50): a fibroin-PEG-mDEX gel group (sampling times: 1 h, day 1, 4, 7, 10, and 14) and an mDEX control group (sampling times: 1, 3, 6, and 12 h). At each sampling point, 5 guinea pigs (3 in the gel group and 2 in the control group) are sampled for analysis. The cerebrospinal fluid (CSF) is extracted by making a midline incision behind the top of the head, peeling the muscle layer to expose the cerebellomedullary cistern and extracting 20 μl CSF using a microsyringe. A blood sample is extracted by cardiac puncture and transferred to a centrifuge tube added with heparin and centrifuged for 5 min (3500 rpm/s). Then, the upper serum (about 100 μl/animal) is transferred to a hollow tube. For perilymph sampling, ex vivo extraction is used in order to avoid contamination of the cerebrospinal fluid. After the tested animal is fully anesthetized, the cochlea is separated from the temporal bone. A small hole is made on the apical turn of the cochlea and the perilymph is extracted with a microsyringe pump (5-7 μl). All samples are stored in a −80° C. environment before examination.

Figure 32:
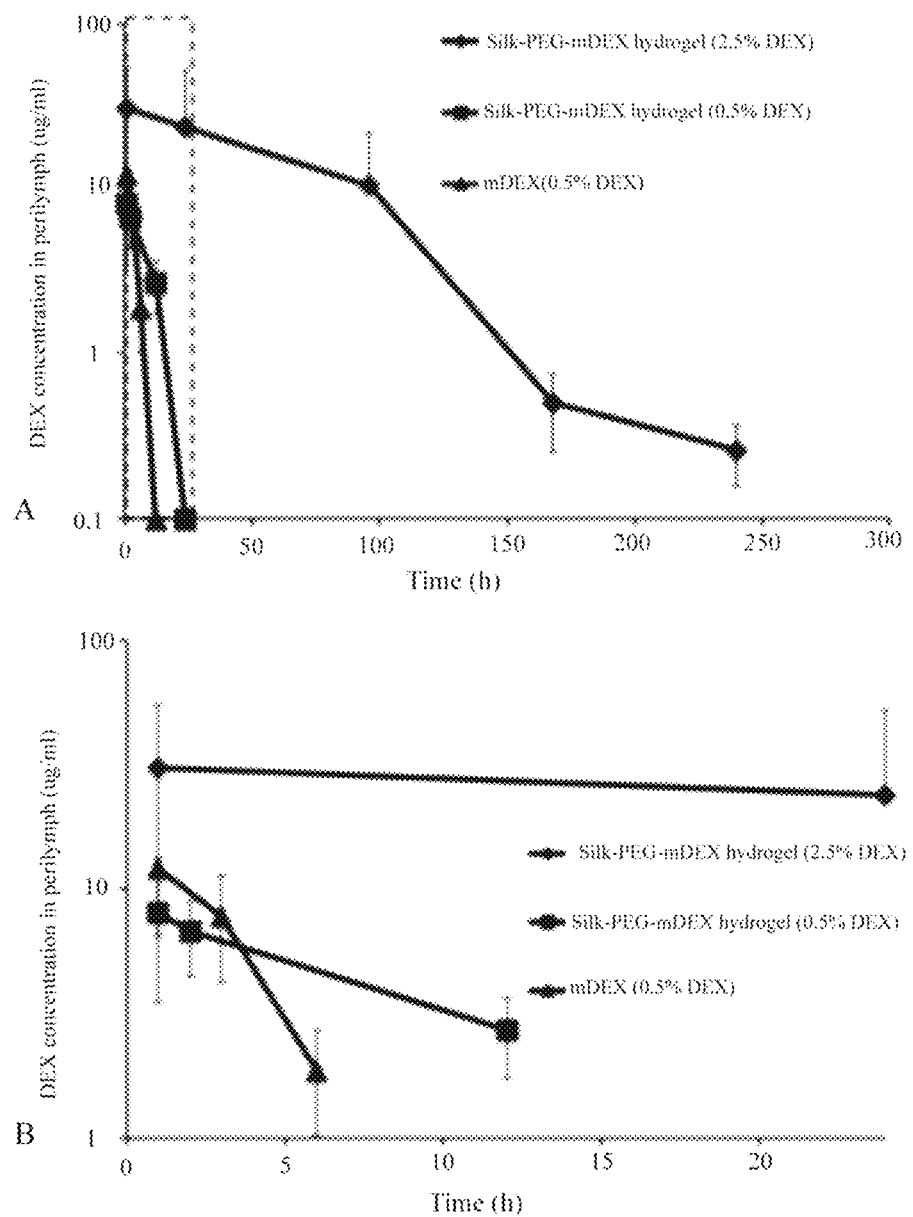
FIG. 32 shows the results of DEX concentration in perilymph at various time points.

Results:
After the silk fibroin-PEG-mDEX gel and the mDEX solution (control group) are injected into the round window membrane of the guinea pigs, the perilymph, CSF and plasma samples of the guinea pigs are sampled periodically for examining the DEX concentration. FIG. 32 shows a comparison of DEX concentration released in the perilymph at various time points, for the silk fibroin-PEG-mDEX gels with a drug loading of 0.5% and 2.5% and the mDEX solution, in which FIG. 32A shows the results for 0-200 h, and FIG. 32B shows a comparison of partial enlargement for the 0-30 h region. As can be seen, in the control group, the DEX concentration in the perilymph reaches a peak at 1 h (13.47±6.02 μg/ml), and decreases to 2.984±1.33 μg/ml at 6 h, and decreases below the detection line at 12 h. In the silk fibroin-PEG-mDEX gel group with a DEX loading of 0.5%, the DEX concentration in the perilymph is 8.06±4.56 μg/ml at 1 h and 2.70±0.97 μg/ml at 12 h, indicating that the DEX release time in this group is longer than that in the control group. When the DEX loading rises to 2.5%, in the silk fibroin-PEG-mDEX group, the time and concentration of DEX in the inner ear are significantly increased, and the detected DEX concentration in the perilymph is 25.71±11.50 μg/ml at 1 h, 6.46±2.89 μg/mh at 4 d, and reaches 0.26±0.15 μg/ml at 10 d. After topical administration, the systemic DEX concentration is very low, and in the silk fibroin-PEG-mDEX (2.5%) group, the detected DEX concentrations in CSF and plasma 1 h after injection into the ear are 0.23±0.10 and 0.032±0.014 µg/ml, respectively. Compared to the concentrations in the perilymph, they are reduced by about 110 and 800 times. DEX cannot be detected after 2 h. In the silk fibroin-PEG-mDEX group with a low loading (0.5%), DEX cannot be detected in both CSF and plasma at 1 h. These results show that the silk fibroin-PEG gel can achieve sustained release of DEX in the cochlea for above 10 days.

(c) Auditory Brainstem Response (ABR)

Method:

In order to evaluate the safety of a silk fibroin-PEG-mDEX gel and the effect of its use in an auditory surgical procedure, the auditory function is assessed by the ABR test at 4 time points: pre-operation, 1 days post-operation, 4 days post-operation, and 14 days post-operation. 12 guinea pigs are divided into 2 groups: an operation control group (without a drug, n=6) and a silk fibroin-PEG-mDEX gel group (n=6). The ABR is analyzed at a particular frequency (4K, 8K, 16K, 24K) by a TDT-II recording system (Alachua, Fla., USA). The tested animals are anesthetized by intraperitoneal injection of 1% pentobarbital (35 mg/kg). The tested animals are placed on a heating pad (38° C.) and tested in a sound proof room. 3 needle electrodes are subcutaneously implanted to measure the activity of the brain stem: one is implanted behind the ear (reference electrode), one is implanted on the top of the skull (working electrode), and one is implanted on the rear leg at the opposite side (ground electrode). The evoked potential is filtered by a band pass filter at 100-300 Hz, 512 times on average. At each given frequency, the tone burst intensity starts at 90 dB SPL and is gradually weaken at 5 dB until it reaches a threshold. The threshold of ABR is located in a band III in which the minimum intensity that can be gathered is reproducible.

Figure 33:
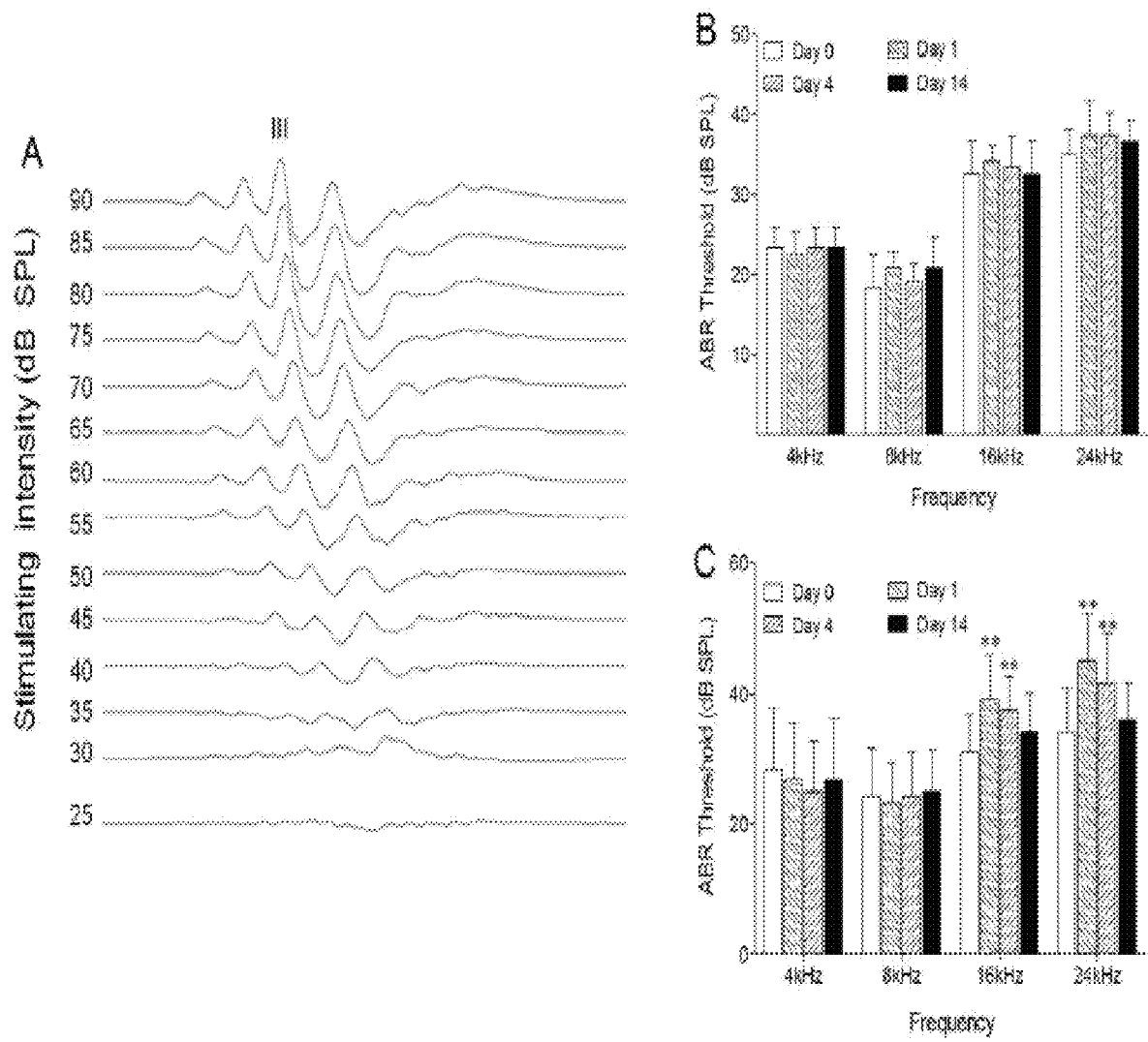
FIG. 33 is a comparison diagram shows the influence on auditory threshold for a sham operation group and a group injected with a silk fibroin-PEG-mDEX gel in the round window membrane.

Results:

The change in threshold with the change in tone burst intensity in the experiment is shown in FIG. 33A. In the operation control group, the auditory function is not affected at all time points (pre-operation, 1 days, 4 days, 14 days) and any frequency (FIG. 33B). In the silk fibroin-PEG-mDEX gel group with a high dosing (2.5%) (FIG. 33C), the hearing at frequency bands of 4 kHz and 8 kHz is unchanged, without the increase in threshold. At frequency bands of 16 K and 24 K, compared to the threshold level pre-operation, the hearing has a temporal small decrease after the gel is injected, and the threshold is increased by 5-15 dB SPL within 1 day (39.2±6.6 vs 30.8±5.8 at 16 k Hz; 45.0±7.1 vs 34.2±6.6 at 24 k Hz, p<0.01). This increase in auditory threshold begins to fade at day 4 (37.5±5.2 vs 30.8±5.8 at 16 k Hz; 41.7±7.5 vs 34.2±6.6 at 24 k Hz, p<0.01) and completely disappears at day 14 (34.2±5.8 vs 30.8±5.8 at 16 k Hz; 35.8±5.8 vs 34.2±6.6 at 24 k Hz, p>0.05), indicating that the effect of gel injection on the auditory function is temporary and will gradually disappear with the degradation of the gel and the release of the drug.

(d) Histological Evaluation

Method:

After tested animals are sacrificed, the cochlea is rapidly separated, perfused with PBS containing 4% paraformaldehyde, and immersed in a fixative at 4° C. overnight. In order to obtain the entire Organ of Corti, the basilar membrane and the Organ of Corti are carefully separated from each other by dissection under a microscope. Hair cells in the ear are stained with rhodamine-phalloidin (1:100) to distinguish the hair cells of the cochlea. Each cochlea is separately examined under a Leica TCS SPE microscope. Each cochlea is counted for 200 µm of cross-sections selected randomly for 3 times. The percentage of active hair cells is obtained by dividing the number of active hair cells by the total number of hair cells (the number of active cells plus inner hair cells). Cochlea sections are prepared by dipping the cochlea and the middle ear in 0.1 M EDTA for 14 days for decalcification and making sections along a longitudinal axis of the cochlea at a section thickness of 7 µm, and are subjected to H&E staining for optical microscopy.

Figure 34:
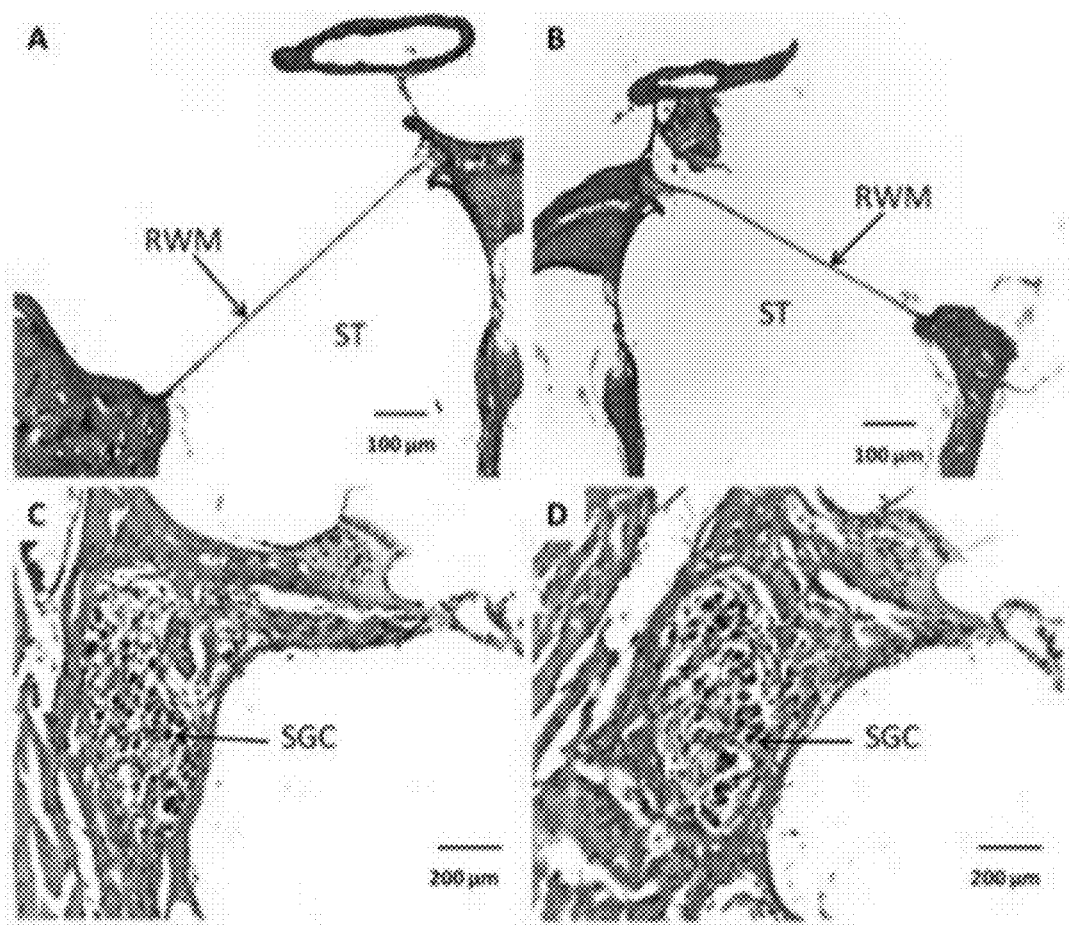
FIG. 34 shows tissue sections of tympanum and inner ear samples in guinea pigs.

Results:

The histological evaluation of the cochlea and the middle ear starts at day 10 post-operation. The important point in analysis is inflammation possibly occurring in the tympanum, round window niche, round window membrane, and scala tympani. Also, the effect of silk fibroin-PEG-mDEX gels on the Organ of Corti and the spiral ganglion is assessed. The results show that there is no significant severe inflammatory response (effusion, edema, fibrosis) in all the groups. Small amounts of inflammatory cells and blood cells may appear in the scala tympani near the round window membrane. However, from a comparison of the number of inflammatory cells between the experimental group (silk fibroin-PEG-mDEX gel, FIG. 34B) and the control group (non-treated for ears, FIG. 34A), there is no significant difference in values. Compared to the control group (mDEX solution group, FIG. 34C), the gel administration group (FIG. 34D) has no any change in size, morphology and number of gangliocytes.

Figure 35:
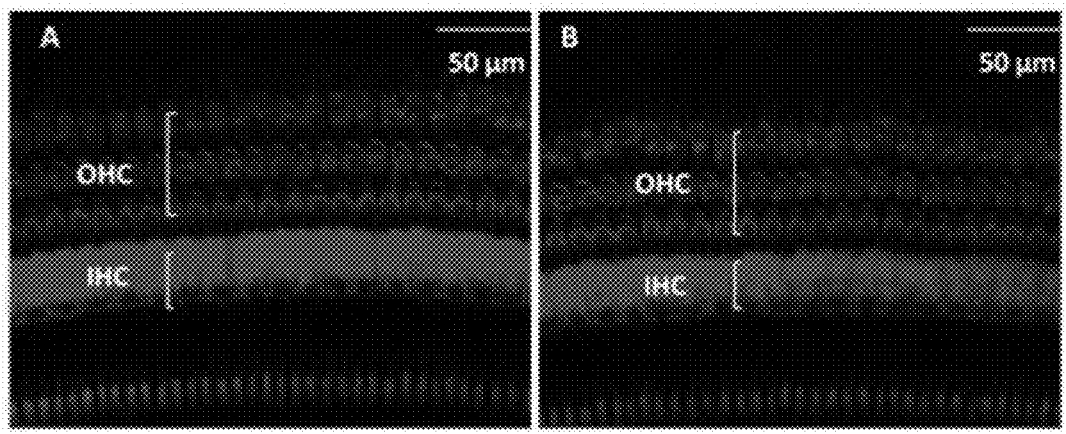
FIG. 35 shows the results of fluorescent staining of basilar membrane using rhodamine-phalloidin staining.

The possibility of loss in inner and outer hair cells after the silk fibroin-PEG-mDEX gel is injected is investigated by observing the histology of the entire surface of the cochlea under a microscope. The quantitative counting analysis in Table 5 shows that there is some loss in outer hair cells for the treatment group and the blank group, but there is no significant difference (p<0.01). As shown in FIG. 35, no changes occur in inner hair cells for all the groups (A: control group; B: treatment group).

TABLE 5

Percentages of active inner hair cells and active outer hair cells at day 10 after injection of the silk fibroin-PEG-mDEX gel (n = 3)

| | Active outer hair cells % | | Active inner hair cells % | |
|---|---|---|---|---|
| | Control | Gel | Control | Gel |
| Basal turn | 99.3 ± 1.5 | 99.3 ± 1.0 | 100 ± 0 | 100 ± 0 |
| Second turn | 98.8 ± 1.5 | 99.1 ± 1.1 | 100 ± 0 | 100 ± 0 |
| Third turn | 97.5 ± 1.7 | 97.7 ± 1.7 | 100 ± 0 | 100 ± 0 |
| Apical turn | 97.0 ± 2.1 | 97.0 ± 3.0 | 100 ± 0 | 100 ± 0 |

(e) Degradation of a Silk Fibroin-PEG-mDEX Gel in Vivo

Method:

Animals are sacrificed 1 h, 4, 7, 10, 14, and 21 days after injection of a gel and the otic vesicle is obtained. The otic vesicle is opened to expose the cochlea, and the silk fibroin-PEG-mDEX gel remaining on the round window niche is observed under a microscope.

Figure 36:
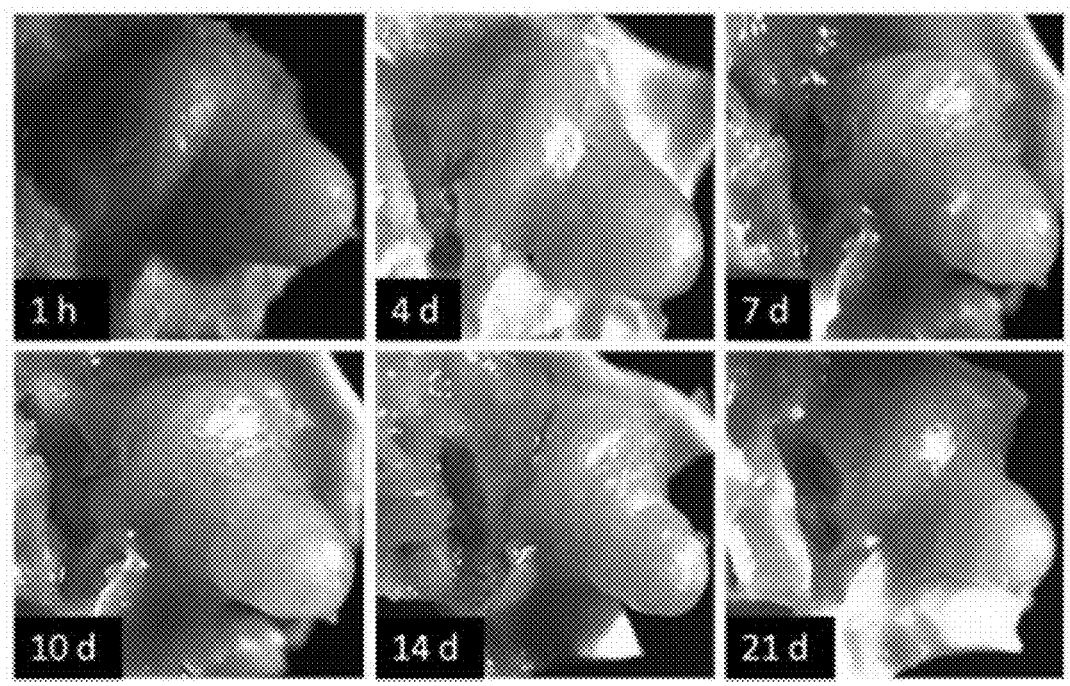
FIG. 36 shows in vivo biodegradation of silk fibroin-PEG-mDEX gels.

Results:

After separation of the otic vesicle, the biodegradability of the silk fibroin-PEG-mDEX gel is monitored by periodical observation under a microscope. FIG. 36 shows the degradation of the silk fibroin-PEG-mDEX gel at 1 h, 4, 7, 10, 14, and 21 days after injection of the gel, in which a red arrow indicates the position of the round window niche and the remaining gel. It can be found that a white stable gel state can be observed in the round window niche at 1 h after injection of the gel, the change in volume of the gel is seen at day 10 and the gel begins to degrade, the decrease in volume of the gel is continued until day 14, and essentially no remaining gel can be seen in the round window niche at day 21.

The above preferred embodiments are described for illustration only, and are not intended to limit the scope of the invention. It should be understood, for a person skilled in the art, that various improvements or variations can be made therein without departing from the spirit and scope of the invention, and these improvements or variations should be covered within the protecting scope of the invention.

What is claimed is:

1. A preparation process of a freeze-dried powder of high molecular weight silk fibroin, comprising the steps of:
   (1) boiling silk in an amount of a sodium carbonate solution for a period of time, and then soaking and washing with clear water to get degummed silk;
   (2) after air drying of the degummed silk, dissolving a suitable amount of the degummed silk in a lithium bromide solution;
   (3) after complete dissolution, dialyzing the degummed silk in a dialysis tube;
   (4) after dialysis, centrifuging the degummed silk, and taking a supernatant; and
   (5) after determining the concentration of the solution, mixing the supernatant with a buffer solution to prepare a silk fibroin solution, treating the silk fibroin solution with high temperature and high pressure, inducing silk fibroin molecules the silk fibroin solution to form nanoparticles, maintaining the molecular weight of the silk fibroin molecules, transferring a volume of the silk fibroin solution into a container and freezing overnight, and then freeze-drying for a period of time to obtain the freeze-dried powder of high molecular weight silk fibroin, wherein the buffer solution in step (5) is a PB buffer;
   wherein the silk fibroin solution has a concentration of 3% w/v or less than 3% w/v; and
   wherein a final concentration of the PB buffer is not less than 5 mM.

2. The preparation process of a freeze-dried powder of high molecular weight silk fibroin of claim 1, wherein the steps (2), (3) and (4) are replaced with the following steps:
   (1') silk dissolution: dissolving the degummed silk with a calcium chloride-containing ternary solution to get a silk fibroin solution;
   (2') renaturation: sequentially dialyzing the silk fibroin solution against protein denaturant solutions with gradient concentrations from high to low, and then dialyzing against water or ultrafiltrating to get a silk fibroin solution.

3. The preparation process of a freeze-dried powder of high molecular weight silk fibroin of claim 2, wherein the protein denaturant is urea, the protein denaturant solutions including urea solutions of 4 M, 2 M and 1 M, and the duration for each dialysis of the silk fibroin solution being 1 to 5 h.

* * * * *